United States Patent
Koya et al.

(10) Patent No.: US 6,861,436 B2
(45) Date of Patent: Mar. 1, 2005

(54) 1-GLYOXYLAMIDE INDOLIZINES FOR TREATING CANCER

(75) Inventors: Keizo Koya, Brookline, MA (US); Lijun Sun, Harvard, MA (US); Mitsunori Ono, Lexington, MA (US); Weiwen Ying, Ayer, MA (US); Hao Li, Brookline, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 136 days.

(21) Appl. No.: 10/244,088

(22) Filed: Sep. 13, 2002

(65) Prior Publication Data

US 2003/0153759 A1 Aug. 14, 2003

Related U.S. Application Data

(60) Provisional application No. 60/322,020, filed on Sep. 13, 2001.

(51) Int. Cl.⁷ .................. A61K 31/44; A61K 31/47; C07D 221/02; C07D 215/38; C07D 215/46
(52) U.S. Cl. .................. 514/299; 514/313; 514/314; 546/112; 546/159; 546/162
(58) Field of Search ................ 546/112, 159, 546/162; 514/299, 313, 314

(56) References Cited

U.S. PATENT DOCUMENTS 6,214,855 B1   4/2001   Gemba et al.

FOREIGN PATENT DOCUMENTS

| EP | 1085021 A1 | 3/2001 | 514/413 |
| EP | 1157704 A1 | 11/2001 | 514/413 |
| GB | 2287706 A | 9/1995 | 514/413 |
| WO | WO99/59999 | 11/1999 | 514/413 |
| WO | WO00/21563 | 4/2000 | 514/413 |

Primary Examiner—Rita Desai
Assistant Examiner—Raymond Covington
(74) Attorney, Agent, or Firm—Hamilton, Brook, Smith & Reynolds, P.C.

(57) ABSTRACT

Disclosed is a compound represented by Structural Formula (I):

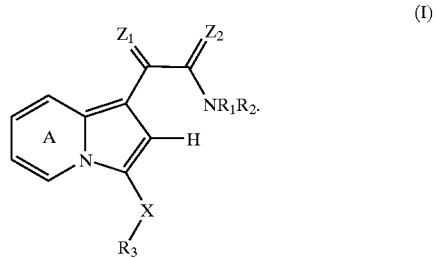

Ring A is substituted or unsubstituted and optionally fused to an aryl group.

$Z_1$ and $Z_2$ are independently =O, =S, =N—$OR_{12}$ or =$NR_{12}$ $R_1$ and $R_2$ are independently —H, an aliphatic group, a substituted aliphatic group, an unsubstituted non-aromatic heterocylic group, a substituted non-aromatic heterocylic group, an aryl group or a substituted aryl group, provided that $R_1$ and $R_2$ are not both —H. Alternatively, —$NR_1R_2$, taken together, is a substituted or unsubstituted non-aromatic nitrogen-containing heterocyclic group or a substituted or unsubstituted nitrogen-containing heteroaryl group.

$R_3$ is a substituted or unsubstituted aryl group or a substituted or unsubstituted aliphatic group.

X is a covalent bond, —C($R_4R_5$)—, —N($R_4$)—, —O—, —S—, —S(O)—, —S(O)$_2$—, —C(=O)—, —C(=O)—N($R_4$)—, or —N($R_4$)—C(=O)—.

$R_4$ and $R_5$ are independently —H or a substituted or unsubstituted aliphatic group.

$R_{12}$ is —H or a substituted or unsubstituted alkyl group.

42 Claims, 2 Drawing Sheets

Anti-Tumor Effects of Compound (1) on MDA435 Xenograft

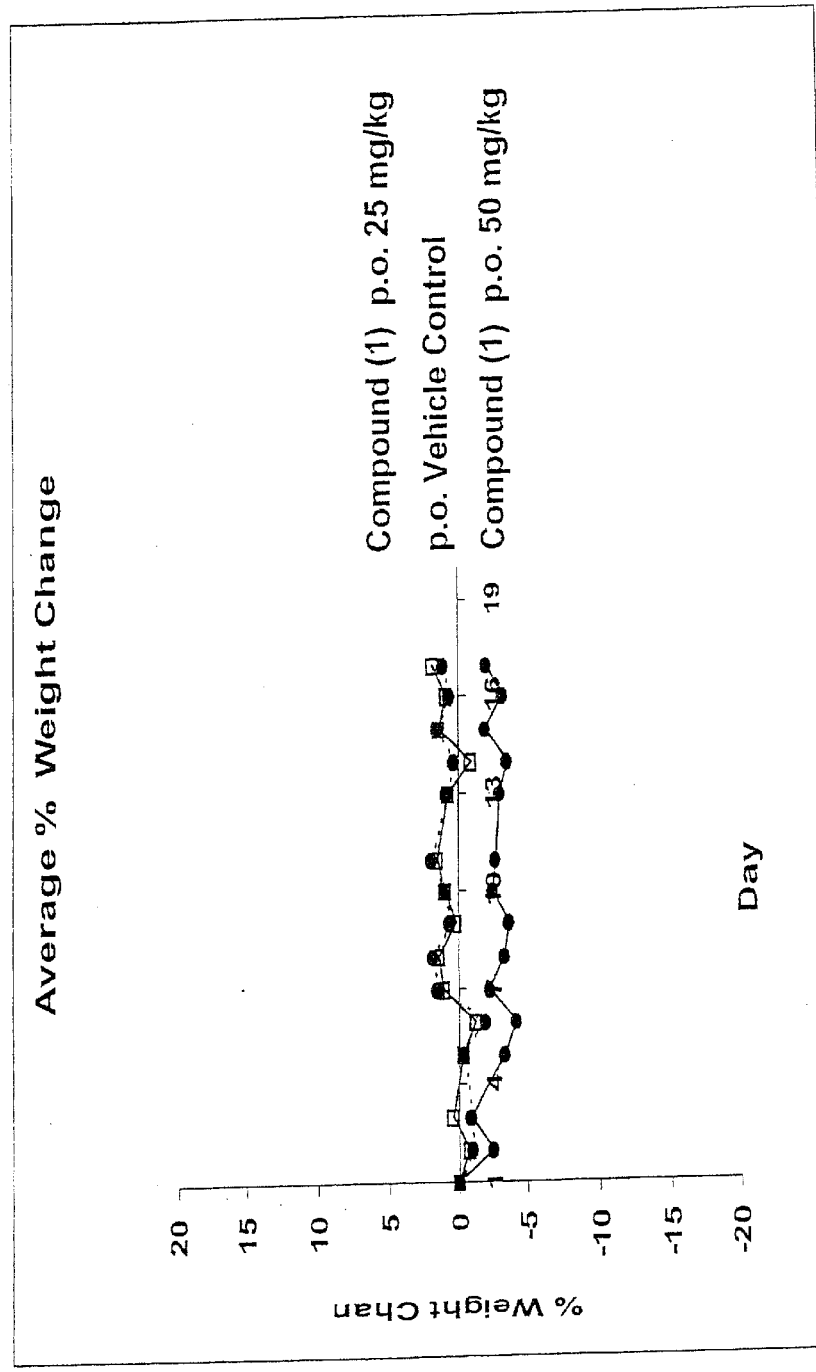
Figure 2. Body Weight Change of Mice on Efficacy Study (MDA 435 Xenograft)

1-GLYOXYLAMIDE INDOLIZINES FOR TREATING CANCER

RELATED APPLICATIONS

This application claims the benefit of U.S. Provisional Application No. 60/322,020, filed Sep. 13, 2001, the entire teachings of which are incorporated herein by reference.

BACKGROUND OF THE INVENTION

Many methods are now available to be used in the treatment of cancer. Despite considerable advances, however, treatments for many cancers are inadequate for a number of reasons.

There are still cancers which simply do not respond or respond poorly to treatments are currently available. Patients with treatable cancers must often undergo chemotherapy with drugs that cause severe side effects. Few of these drugs can be used orally. Perhaps the most serious problem associated with cancer chemotherapy is the development of multi-drug resistance by many tumors. For example, many tumors which initially respond positively to an anti-cancer therapy by decreasing in size or even going into remission often develop resistance to the drug. Tumors that have developed resistance to more than one drug are said to be a "multi-drug resistant". There is little that can be done to halt or retard further progression of the disease, once a patient's cancer has become multi-drug resistant.

There is therefore still a need for new drugs which overcome one or more of the aforementioned shortcomings of drugs currently used in the treatment of cancer. Desirable properties of new anti-cancer drugs therefore include efficacy against tumors that are currently untreatable or poorly treatable, efficacy against multi-drug resistant tumors, oral bioavailability and/or reduced side effects.

SUMMARY OF THE INVENTION

It has now been found that 1-glyoxylamideindolizines are cytotoxic against cancer cells, including multi-drug resistant cancer cells, from a number of different tissue types. For example, the $IC_{50}$ of Compounds (1)–(8) against the multi-drug resistant human uterine sarcoma cell line MES-SA/DX5 and the human myeloid leukemia cell line HL60/TX1000 was less than 0.1 $\mu$M (see Example 9–10 and 12). The structures of these compounds are shown in Example 2. In addition, the volume of tumors from the human breast cancer cell line MDA435 in nude mice was reduced by greater than 50%

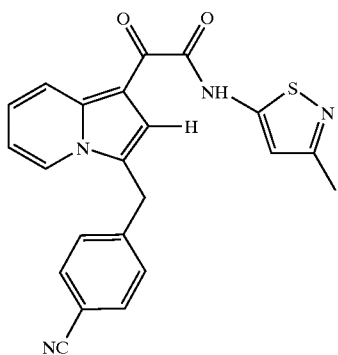

Compound (1)

when Compound (1) was administered orally (Example 11). Little or no change in body weight was observed in mice treated with Compound 1, indicating that the compound caused minimal side-effects. Based on these results, novel 1-glyoxlylamideindolizines, pharmaceutical compositions comprising these 1-glyoxlylamideindolizines, methods of treating subjects with cancer by administering 1-glyoxlylamideindolizines and methods of preparing 1-glyoxlylamideindolizines are disclosed herein.

One embodiment of the present invention is a compound represented by Structural Formula (I):

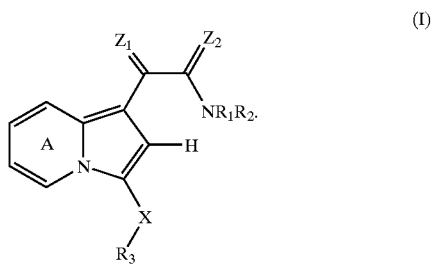

(I)

Ring A is substituted or unsubstituted and is optionally fused to an aryl group (preferably substituted or unsubstituted phenyl).

$Z_1$ and $Z_2$ are independently =O, =S, =N—$OR_{12}$ or =$NR_{12}$.

$R_1$ and $R_2$ are independently —H, an aliphatic group, a substituted aliphatic group, an unsubstituted non-aromatic heterocylic group, a substituted non-aromatic heterocylic group, an unsubstituted aryl group or a substituted aryl group, provided that $R_1$ and $R_2$ are not both —H. Alternatively, —$NR_1R_2$, taken together, is a substituted or unsubstituted non-aromatic nitrogen-containing heterocyclic group or a substituted or unsubstituted nitrogen-containing heteroaryl group.

$R_3$ is a substituted or unsubstituted aryl group or a substituted or unsubstituted aliphatic group.

X is a covalent bond, —C($R_4R_5$)—, —N($R_4$)—, —O—, —S—, —S(O)—, —S(O)$_2$—, —C(=O)—, —C(=O)—N($R_4$)—, or —N($R_4$)—C(=O)—.

$R_4$ and $R_5$ are independently —H or a substituted or unsubstituted aliphatic group.

$R_{12}$ is —H or a substituted or unsubstituted alkyl group.

Another embodiment of the present invention is a pharmaceutical composition comprising a pharmaceutically acceptable carrier or diluent and a compound represented by Structural Formula (I). Preferably, the pharmaceutical composition comprises an effective amount of the compound. The pharmaceutical compositions can be used in therapy, for example, to treat a subject with cancer.

Another embodiment of the present invention is the use of a compound represented by Structural Formula (I) for the manufacture of a medicament for the treatment of a subject with cancer. The medicament comprises an effective amount of the compound.

Another embodiment is a method of treating a subject with cancer. The method comprises administering to the subject an effective amount of a compound represented by Structural Formula (I).

Another embodiment is a method of preparing an intermediate in the synthesis of the compound represented by Structural Formula (I). The intermediate is represented by Structural Formula (Ia):

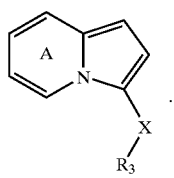

(Ia)

The method comprises the step of reacting a Cu$^I$ salt with a precursor compound represented by Structural Formula (Ib):

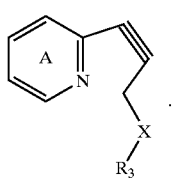

(Ib)

In Structural Formula (Ia) and (Ib), Ring A, X, $R_3$, $R_4$ and $R_5$ are as described for Structural Formula (I), provided, however, that when X is —C($R_4R_5$)—, then $R_3$ in Structural Formulas (Ia) and (Ib) is not a substituted or unsubstituted aliphatic group.

The disclosed 1-glyoxlylamideindolizines have many advantages when used to treat cancers. Most significantly, they are cytotoxic to many multi-drug resistant cell lines and therefore can be used when other traditional cancer chemotherapies have failed. In addition, they exhibit minimal side effects and are active when administered orally.

BRIEF DESCRIPTION OF THE DRAWINGS

FIG. 2 is graph showing the percent weight change in nude mice being administered vehicle, 25 mg/kg Compound (1) and 50 mg/kg Compound (1) over time in days.

DETAILED DESCRIPTION OF THE INVENTION

Figure 1:
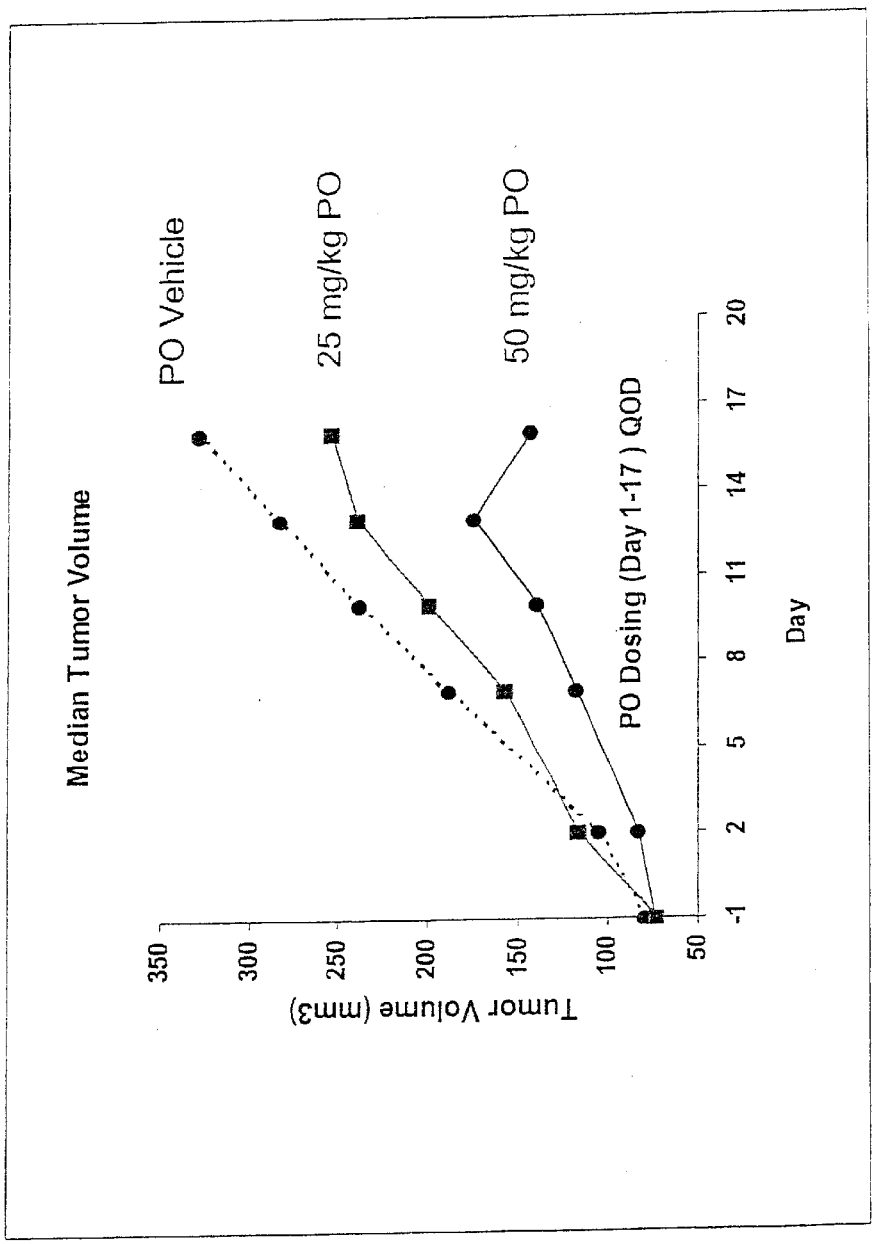
FIG. 1 is a graph depicting the anti-tumor effects of Compound (1) administered orally to nude mice with human breast MDA435 tumors. The graph show the volume of the tumors in mm$^3$ over time in days after the beginning of dosing with vehicle, 25 mg/kg Compound (1) and 50 mg/kg Compound (1).

In a preferred embodiment, the compound of the present invention is represented by Structural Formula (I) wherein Ring A is a substituted or unsubstituted aryl group; $Z_1$ and $Z_2$ are both =O; $R_1$ is —H; $R_2$ is a substituted or unsubstituted alkyl or aryl group; $R_3$ is a substituted or unsubstituted aryl group; X is —C($R_4R_5$)—, —N($R_4$)— or —O— (preferably, X is —C($R_4R_5$)—); and $R_4$, $R_5$, $Z_1$ and $Z_2$ are as described above. More preferably, $R_3$ is a substituted or unsubstituted phenyl or pyridyl group; and $R_4$ and $R_5$ are both —H.

As noted above, values for $R_1$-$R_3$ include substituted and unsubstituted aryl group. For $R_2$, preferred aryl groups are represented by Structural Formulas (II)–(XV):

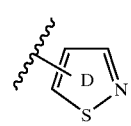

(II)

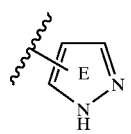

(III)

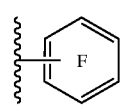

(IV)

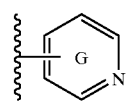

(V)

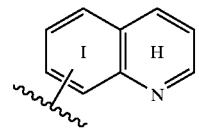

(VI)

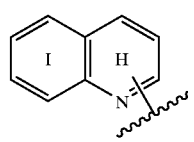

(VII)

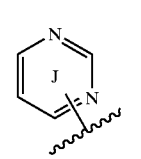

(VIII)

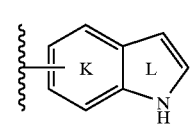

(IX)

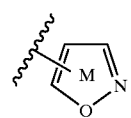

(X)

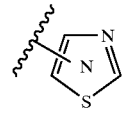

(XI)

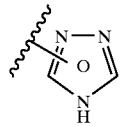

(XII)

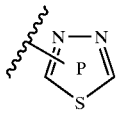

(XIII)

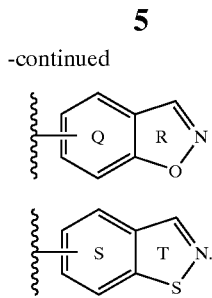

(XIV)

(XV)

Rings D–T are substituted or unsubstituted. More preferred aryl groups for $R_2$ are represented by Structural Formulas (XVI)–(XXI):

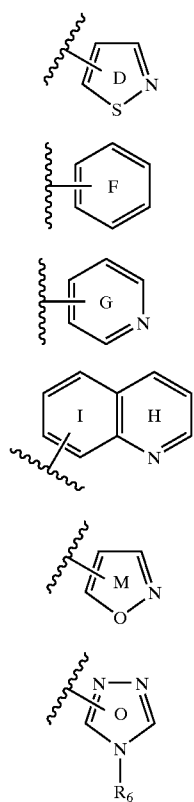

(XVI)

(XVII)

(XVIII)

(XIX)

(XX)

(XXI)

$R_6$ is —H or a substituted or unsubstituted alkyl group and Rings D, F, G, I, H, M and O are as described above.

Even more preferred aryl groups for $R_2$ are represented by Structural Formulas (XXII)–(XXVII):

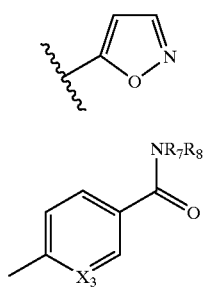

(XXII)

(XXIII)

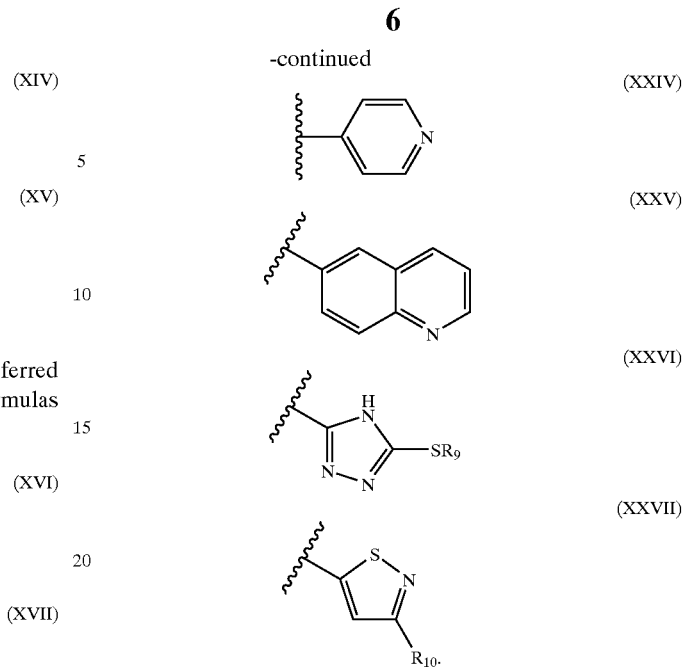

(XXIV)

(XXV)

(XXVI)

(XXVII)

$X_3$ is —CH— or —N—.

$R_7$ and $R_8$ are independently —H or an alkyl group. Alternatively, —$NR_7R_8$, taken together, is a nitrogen-containing non-aromatic heterocyclic group.

$R_9$ is an alkyl group.

$R_{10}$ is —H or an alkyl group.

In another preferred embodiment, the compound of the present invention is represented by Structural Formula (XXVIII):

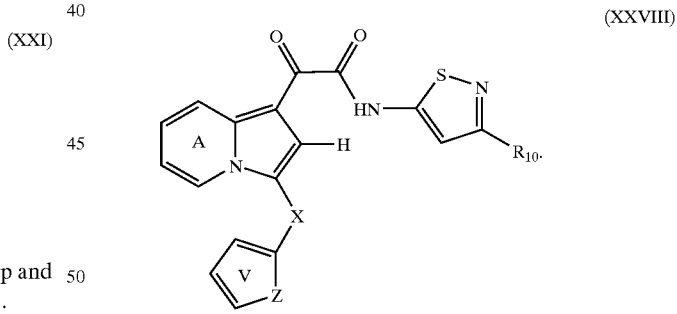

(XXVIII)

In Structural Formula (XXVIII), Rings A and V are independently substituted or unsubstituted; X is —$CH_2$—, —$CH(CH_3)$—, —O—, —NH— or —$NCH_3$—; Z is —O—, —S—, —NR—, —C≡C—, —CH=N—, —N=CH—, —N=N—; R is —H or $C1-C_4$ alkyl; and $R_{10}$ is —H, an unsubstituted aliphatic group or a substituted aliphatic group. Even more preferably, Ring A is unsubstituted, Ring V is substituted with one or more groups represented by $R_{11}$, wherein each $R_{11}$ is independently —$CH_3$, —$CH_2CH_3$, —$OCH_3$, —F, —Cl or —CN.

In a more preferred embodiment, the compound of the present invention is represented by Structural Formula (XXIX):

(XXIX)

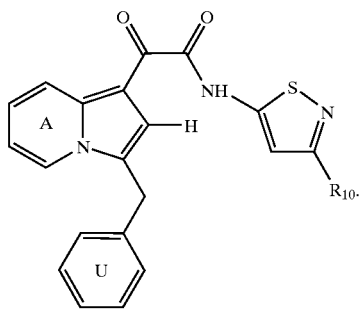

In Structural Formula (XXIX), Rings A and U are independently substituted or unsubstituted and $R_{10}$ is —H, an unsubstituted aliphatic group or a substituted aliphatic group. Even more preferably, Ring A is unsubstituted, Ring U is substituted with one or more groups represented by $R_{11}$, wherein each $R_{11}$ is independently —$CH_3$, —$CH_2CH_3$, —$OCH_3$, —F, —Cl or —CN. Preferably, $R_{11}$ is in the para position relative to the carbon bonded to the methylene group.

The term "aryl group" refers to carbocyclic aromatic groups such as phenyl, naphthyl, and anthracyl, and heteroaryl groups such as imidazolyl, isoimidazolyl, thienyl, furanyl, pyridyl, pyrimidyl, pyranyl, pyrazolyl, pyrrolyl, pyrazinyl, thiazoyl, isothiazolyl, oxazolyl, isooxazolyl, 1,2, 3-trizaolyl, 1,2,4-triazolyl, and tetrazolyl.

Aryl groups also include fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazolyl, benzoisothiazolyl, benzooxazolyl, benzoisooxazolyl, benzimidazolyl, quinolinyl, isoquinolinyl and isoindolyl.

An aliphatic group is a straight chained, branched or cyclic non-aromatic hydrocarbon which is completely saturated or which contains one or more units of unsaturation. Typically, a straight chained or branched aliphatic group has from 1 to about 10 carbon atoms, preferably from 1 to about 4, and a cyclic aliphatic group has from 3 to about 10 carbon atoms, preferably from 3 to about 8. An aliphatic group is preferably a straight chained or branched alkyl group, e.g., methyl, ethyl, n-propyl, iso-propyl, n-butyl, sec-butyl, tert-butyl, pentyl, hexyl, pentyl or octyl, or a cycloalkyl group with 3 to about 8 carbon atoms. A C1–C4 straight chained or branched alkyl group or a C3–C8 cyclic alkyl group is also referred to as a "lower alkyl" group.

An "alkylene group" is represented by —$(CH_2)_n$—. n is an integer from 1–10, preferably 1–4.

Non-aromatic heterocyclic rings are non-aromatic carbocyclic rings which include one or more heteroatoms such as nitrogen, oxygen or sulfur in the ring. The ring can be five, six, seven or eight-membered. Examples include oxazolinyl, thiazolinyl, oxazolidinyl, thiazolidinyl, tetrahydrofuranyl, tetrahyrothiophenyl, morpholino, thiomorpholino, pyrrolidinyl, piperazinyl, piperidinyl, and thiazolidinyl.

Suitable substituents for an aliphatic group, non-aromatic heterocyclic group, benzylic or an aryl group ring carbon (carbocyclic and heteroaryl) are those which do not substantially interfere with the anti-cancer activity of the disclosed compounds. Examples of suitable substituents include —OH, halogen (—Br, —Cl, —I and —F), —$OR^3$, —O—$COR^a$, —$COR^a$, —CN, —$NO_2$, —COOH, —$SO_3H$, —$NH_2$, —$NHR^a$, —$N(R^aR^b)$, —$COOR^a$, —CHO, —$CONH_2$, —$CONHR^a$, —$CON(R^aR^b)$, —$NHCOR^a$, —$NRCOR^a$, —$NHCONH_2$, —$NHCONR^aH$, —$NHCON(R^aR^b)$, —$NR^cCONH_2$, —$NR^cCONR^aH$, —$NR^cCON(R^aR^b)$, —C(=NH)—$NH_2$, —C(=NH)—$NHR^a$, —C(=NH)—$N(R^aR^b)$, —C(=$NR^c$)—$NH_2$, —C(=$NR^c$)—$NHR^a$, —C(=$NR^c$)—$N(R^aR^b)$, —NH—C(=NH)—$NH_2$, —NH—C(=NH)—$NHR^a$, —NH—C(=NH)—$N(R^aR^b)$, —NH—C(=$NR^c$)—$NH_2$, —NH—C(=$NR^c$)—$NHR^a$, —NH—C(=$NR^c$)—$N(R^aR^b)$, —$NR^d$H—C(=NH)—$NH_2$, —$NR^d$—C(=NH)—$NHR^a$, —$NR^d$—C(=NH)—$N(R^aR^b)$, —$NR^d$—C(=$NR^c$)—$NH_2$, —$NR^d$—C(=$NR^c$)—$NHR^a$, —$NR^d$—C(=$NR^c$)—$N(R^aR^b)$, —$NHNH_2$, —$NHNHR^a$, —$NHR^aR^b$, —$SO_2NH_2$, —$SO_2NHR^a$, —$SO_2NR^aR^b$, —CH=$CHR^a$, —CH=$CR^aR^b$, —$CR^c$=$CR^aR^b$, —$CR^c$=$CHR^a$, —$CR^c$=$CR^aR^b$, —$CCR^a$, —SH, —$SO_kR^a$ (k is 0, 1 or 2) and —NH—C(=NH)—$NH_2$, $R^a$–$R^d$ are each independently an aliphatic, substituted aliphatic, benzyl, substituted benzyl, aryl or substituted aryl group, preferably an alkyl, benzylic or aryl group. In addition, —$N(R^aR^b)$, taken together, can also form a substituted or unsubstituted non-aromatic heterocyclic group. A non-aromatic heterocyclic group, benzylic group or aryl group can also have an aliphatic or substituted aliphatic group as a substituent. A substituted aliphatic group can also have a non-aromatic heterocyclic ring, a substituted a non-aromatic heterocyclic ring, benzyl, substituted benzyl, aryl or substituted aryl group as a substituent. A substituted aliphatic, non-aromatic, heterocyclic group, substituted awl, or substituted benzyl group can have more than one substituent.

Suitable substituents for heteroaryl ring nitrogen atoms having three covalent bonds to other heteroaryl ring atoms include —OH and -alkoxy (preferably C1–C4). Substituted heteroaryl ring nitrogen atoms that have three covalent bonds to other heteroaryl ring atoms are positively charged, which is balanced by counteranions such as chloride, bromide, formate, acetate and the like. Examples of other suitable counteranions are provided in the section below directed to suitable pharmacologically acceptable salts.

Suitable substituents for heteroaryl ring nitrogen atoms having two covalent bonds to other heteroaryl ring atoms include alkyl, substituted alkyl (including haloalkyl), phenyl, substituted phenyl, —$S(O)_2$-(alkyl), —$S(O)_2$—NH (alkyl) and —$S(O)_2$—NH(alkyl)$_2$.

Preferred substituents for Ring A include —F, —Cl, —Br, —C1–C4 alkyl, C1–C4 alkoxy, —C1–C4 haloalkyl, C1–C4 haloalkoxy, —CN or —$NH_2$. Ring A can have zero, one or more substituents.

Preferred substitutents for Rings D–T include C1–C4 alkyl, C1–C4 hydroxyalkyl, N-morpholino, pyrimidyl, C1–C4 alkyl substituted with pyrimidyl, —N(C1–C4 alkyl)$_2$, —$C(O)NH_2$, —C(O)NH(C1–C4 alkyl), C(O)N (C1–C4 alkyl)$_2$, —NHC(O)(C1–C4 alkyl) —$NO_2$, C1–C4 alkoxy, —C(O)O—$CH_2CH_2$—N(C1–C4 alkyl)$_2$,

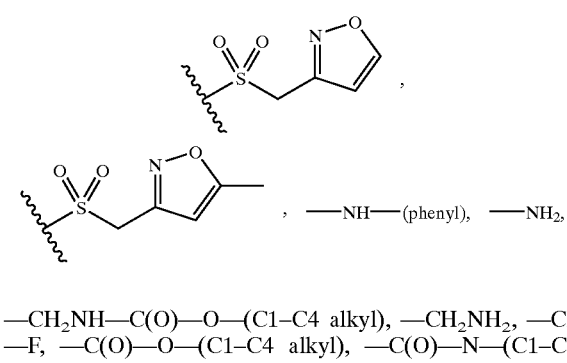

, —NH—(phenyl), —$NH_2$,

—$CH_2NH$—C(O)—O—(C1–C4 alkyl), —$CH_2NH_2$, —Cl, —F, —C(O)—O—(C1–C4 alkyl), —C(O)—N—(C1–C4 alkyl), C3–C7 cycloalkyl, phenyl, —C(O)—N-morpholino, —S—(C1–C4 alkyl), —CN, furyl, —S(O)$_2$—(C1–C4 alkyl), —S(O)$_2$—NH$_2$, —S(O)$_2$—NH(C1–C4 alkyl) or —S(O)$_2$—N(C1–C4 alkyl)$_2$.

Preferred substituents for Ring U, Ring V and the phenyl and pyridyl ring represented by R$_3$ include —Br, —Cl, —F, —R$^e$, —OR$^e$, —CN, —COOR$^e$, —N(R$^e$)$_2$, —CON(R$^e$)$_2$, —NR$^e$COR$^f$, —NHCONH$_2$ and —SO$_2$ N(R$^e$)$_2$. Each R$^e$ and R$^f$ are independently selected from —H, alkyl or substituted alkyl. More preferred substituents for Ring U, Ring V and the phenyl group represented by R$_3$ include —Cl, —F, —R$^e$, —OR$^e$, —CN, —NH$_2$, —CONH$_2$ or —NHCOR$^f$. Even more preferred substituents for Ring U, Ring V and the phenyl group represented by R$_3$ include —CH$_3$, —CH$_2$CH$_3$, —F, —Cl, —CN or —OCH$_3$. Ring U, Ring V and the phenyl and pyridyl ring represented by R$_3$ can have zero, one or more substituents, but are preferably unsubstituted or monosubstituted substituted. When Ring U, Ring V and R$_3$ are a six-membered aromatic ring and monosubstituted, the substituent is preferably at the position para to the carbon atom bonded to the methylene group.

Also included in the present invention are pharmaceutically acceptable salts of the compounds described herein. Compounds disclosed herein which possess a sufficiently acidic, a sufficiently basic, or both functional groups, and accordingly can react with any of a number of organic or inorganic bases, and inorganic and organic acids, to form a salt. Acids commonly employed to form acid addition salts from compounds with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

The disclosed compounds can be used to treat subjects with cancer, including multi-drug resistant cancers. A cancer is resistant to a drug when it resumes a normal rate of tumor growth while undergoing treatment with the drug after the tumor had initially responded to the drug. A tumor "responds to a drug" when it exhibits a decrease in tumor mass or a decrease in the rate of tumor growth. The term "multi-drug resistant cancer" refers to cancer that is resistant to two or more drugs, typically five or more.

An "effective amount" is the quantity of compound in which a beneficial clinical outcome is achieved when the compound is administered to a subject with a multi-drug resistant cancer. A "beneficial clinical outcome" includes a reduction in tumor mass, a reduction in the rate of tumor growth, a reduction in metastasis, a reduction in the severity of the symptoms associated with the cancer and/or an increase in the longevity of the subject compared with the absence of the treatment. The precise amount of compound administered to a subject will depend on the type and severity of the disease or condition and on the characteristics of the subject, such as general health, age, sex, body weight and tolerance to drugs. It will also depend on the degree, severity and type of cancer. The skilled artisan will be able to determine appropriate dosages depending on these and other factors. Effective amounts of the disclosed compounds typically range between about 1 mg/mm$^2$ per day and about 10 grams/mm$^2$ per day, and preferably between 10 mg/mm$^2$ per day and about 5 grams/mm$^2$.

The disclosed compounds are administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compounds can also be administered orally (e.g., dietary), topically, by inhalation (e.g., intrabronchial, intranasal, oral inhalation or intranasal drops), or rectally, depending on the type of cancer to be treated. Oral or parenteral administration are preferred modes of administration.

The disclosed compounds can be administered to the subject in conjunction with an acceptable pharmaceutical carrier as part of a pharmaceutical composition for treatment of cancer. Formulation of the compound to be administered will vary according to the route of administration selected (e.g., solution, emulsion, capsule). Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextrasn) are known in the art (Baker, et al., "Controlled Release of Biological Active Agents", John Wiley and Sons, 1986).

Optionally, the disclosed compounds can be co-administered with other anticancer agents such as Taxol, Vincristine, Adriamycin, Etoposide, Doxorubicin. Dactinomycin, Mitomycin C, Bleomycin, Vinblastine, Cisplatin and the like. Preferably, the disclosed compounds are co-administered before the cancer develops multi-drug resistance or as the cancer is developing multi-drug resistance but before the cancer becomes completely resistant to the anticancer drugs being used. The method can also be carried in combination with other cancer treatments such as surgery, radiation, and the like.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The compound represented by Structural Formula (Ia) is an intermediate in the synthesis of the disclosed 1-glyoxlylindolizines. One method of preparing this intermediate is shown below in Scheme 1:

Scheme 1

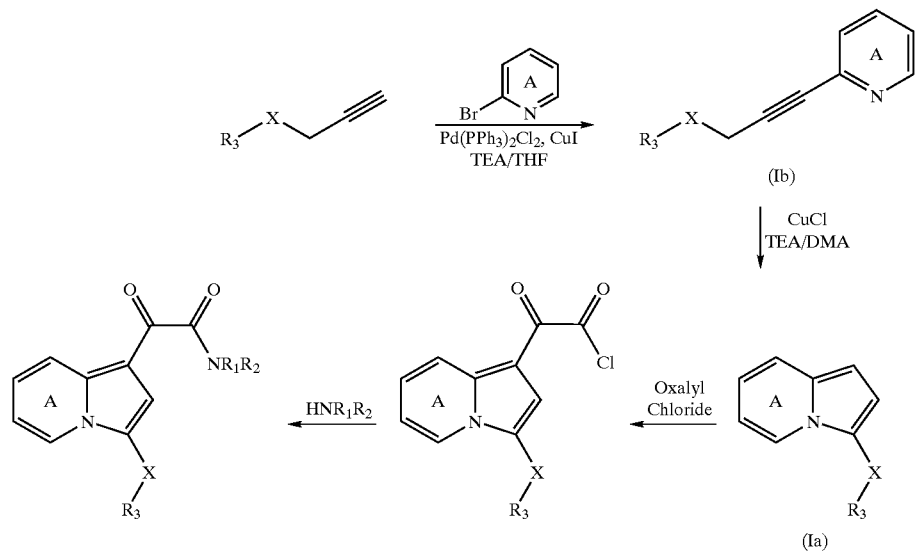

The intermediate represented by Structural Formula (Ia) is prepared by cyclizing the precursor compound represented by Structural Formula (Ib). The cyclization reaction is carried out in the presence of a $Cu^I$ salt such as CuI, CuBr, CuCl, Cu(triflate) and the like. CuCl is the most commonly used $Cu^I$ salt. Typically, equimolar amounts of the $Cu^I$ salt and the precursor compound are used. However, it is also common to use an excess of the $Cu^I$ salt, for example up to a five fold molar excess, more commonly up to a three fold molar excess, and preferably no more than a 50% molar excess. Suitable solvents for this reaction include polar aprotic solvents such as dimethylacetamide (DMA), dimethylformamide (DMF), dimethylsulfoxide (DMSO), hexamethylphosphoramide (HMPA) and N-methylpyrollidinone (NMO). The reaction is typically carried out at elevated temperatures, e.g., between 70° C. and the boiling point of the solvent, preferably between 100° C. and 160° C. and more preferably between 120° and 140° C. A tertiary amine is typically added to the reaction mixture as a co-solvent, typically in amounts between 1:20 and 4:1 v/v relative to the polar aprotic solvent, more typically between 1:10 and 1:1 v/v. Examples of suitable tertiary amines include triethyl amine, diisopropylethylamine, dimethylaniline, dimethylaminopyridine and the like. Triethylamine is most commonly used. Specific examples of conditions used to carry out this reaction are provided in Example 3.

The next step in the synthesis of the disclosed 1-glyoxlylindolizines according to the Scheme 1 is the acylation of the intermediate represented by Structural Formula (Ia) with oxalyl chloride or a synthetic equivalent thereof (e.g., oxalyl bromide). Although equimolar amounts intermediate and acylating agents can be used, typically the acylating agent is used in excess, for example, up to a twenty fold molar excess, preferably up to a ten fold molar excess and more preferably up to a three fold molar excess. Ethereal solvents (e.g., diethyl ether, tetrahydrofuran, 1,4-dioxane, glyme, diglyme and methyl tert-butyl ethyl) and aromatic solvents (e.g., benzene, toluene and xylene) are commonly used. Suitable reaction temperatures range from −50° C. to the boiling point of the solvent and more typically range from −10° C. to room temperature and preferably between −10° C. to 10° C. Specific examples of conditions used to carry out this reaction are provided in Example 3.

The synthesis of the disclosed 1-glyoxlylindolizines according to the Scheme 1 is completed by reacting the acylated intermediate with amine $HNR_1R_2$, wherein $R_1$ and $R_2$ are as described above. The acylated intermediate and the amine are mixed in a suitable solvent, e.g., an ethereal solvent or aromatic solvent. Suitable reaction temperatures are as described above for the acylation reaction. Although an excess of one reactant can be used (e.g., up to a ten fold molar excess), more typically between a 20% molar and 100% molar excess. When less than two equivalents of amine $HNR_1R_2$ are used, a tertiary amine such as triethylamine or dimethylaminopyridine is generally added so that at least two equivalents of amine are present in the reaction mixture relative to the acylated intermediate. Specific examples of conditions used to carry out this reaction are provided in Example 3.

Scheme 2, shown below, shows a second method for preparing certain intermediates represented by Structural Formula (Ia). In Scheme 2, an intermediate designated (100) is cyclized with a reagent prepared from dimethylformamide and dimethylsulfate, or, alternatively, dimethylformamide di-tert-butylacetal. This reaction is described more fully in co-pending U.S. Provisional Application Ser. No. 60/410,679 entitled "Method for Preparing 3-Acyl-Indolizines," filed on Sep. 13, 2002, the entire teachings of which are incorporated herein by reference. Specific conditions for carrying out this reaction are provided in Example 6.

Scheme 2

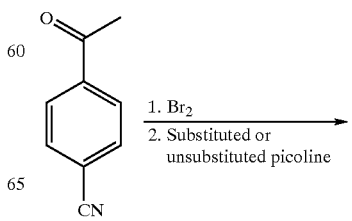

1. $Br_2$
2. Substituted or unsubstituted picoline

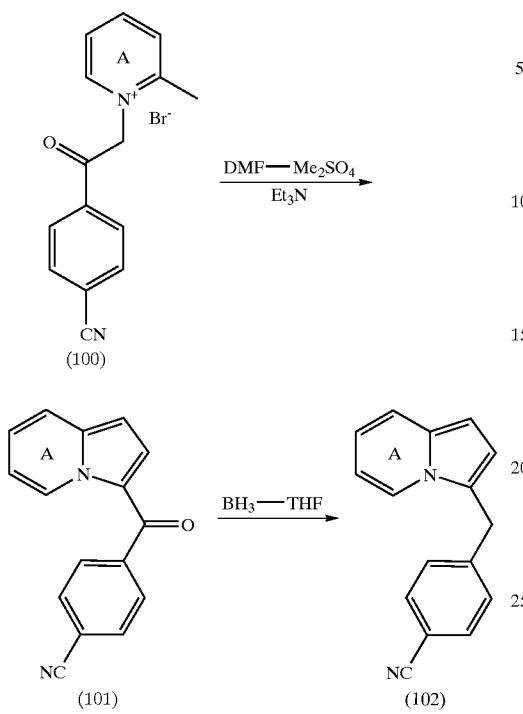

Although the reactions in Scheme 2 are shown with respect to preparing a compound in which the position corresponding to $R_3$ in Structural Formulas (I) and (Ia) is para-cyano phenyl, compounds with other values for $R_3$ can be prepared by a suitable selection of starting materials and conditions.

Scheme 3, shown below, shows a third method for preparing certain compounds represented by Structural Formula (Ia). Specific conditions for carrying out these transformation are provided in Example 1.

Scheme 3

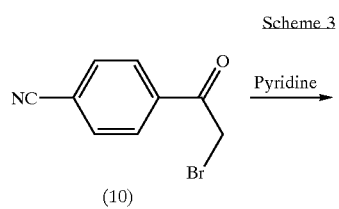

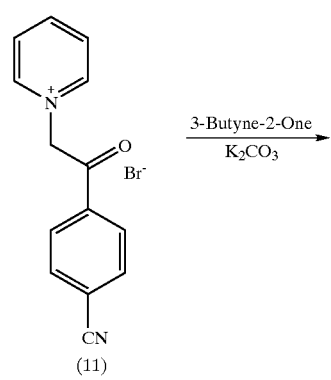

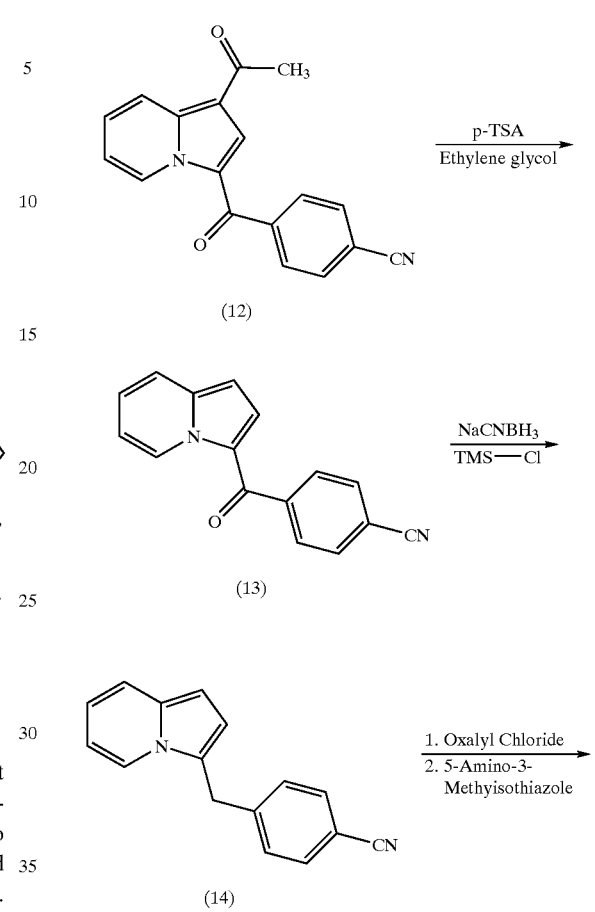

In Scheme 3, "p-TSA" refers to para-toluenesulfonic acid"; "NaCNBH$_3$" refers to sodium cyanoborohydride; and "TMS-Cl" refers to chlorotrimethylsilane. Although the reactions in Scheme 3 are described with respect to preparing Compound (1), other indolizine compounds of the present invention can be readily prepared by suitable selection of the starting materials and reaction conditions.

The present invention is illustrated by the following examples, which are not intended to be limiting in any way.

EXEMPLIFICATION

Example 1

Preparation of 2-(3-(4-cyano-benzyl)-indolizin-1-yl)-N-(3-methyl-isothiazol-5-yl)-2-oxo-acetamide By the Method of Scheme 3

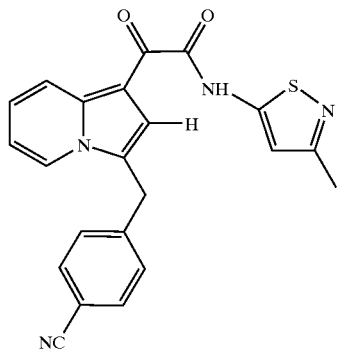

To a solution of 4-cyanophenacyl bromide (10) (5.02 g, 22.2 mmol) in anhydrous acetonitrile (300 mL) was added pyridine (3.6 mL, 45.3 mmol) at room temperature. The mixture was stirred for 30 minutes. The precipitate was filtered, washed with acetonitrile (20 mL) and dried under vacuum to give 1-(2-(4-cyano-phenyl)-2-oxo-ethyl)-pyridinium bromide (11) as a white powder (100%). $^1$H NMR (DMSO-$d_6$) δ 6.56 (s, 2H), 8.21 (m, 6H), 8.76 (t, J=7.8, 1H), 9.03 (d, J=6.6, 2H).

A slurry of 1-(2-(4-cyano-phenyl)-2-oxo-ethyl)-pyridinium bromide (11) (4.04 grams, 13.2 mmol) and potassium carbonate (2.21 grams, 16.0 mmol) in tetrahydrofuran (250 mL) was stirred at room temperature for 10 minutes. To it was added 3-butyn-2-one (1.4 mL, 16.0 mmol), and the reaction mixture was kept stirring at room temperature for 6 hours. The insoluble material was filtered off and the filtrate was concentrated in vacuo. The residue was subjected to column chromatographic purification on silica gel using 3:1 hexane and ethyl acetate ($R_f$ 0.2) to afford 1-acetyl-3-(4-cyanobenzoyl)indolizine (12) as a yellow solid (2.55 grams, 72%). $^1$H NMR (CDCl$_3$) δ 2.56 (s, 3H), 7.23 (m, 1H), 7.62 (m, 2H), 7.90 (m, 4H), 8.72 (d, J=9.0, 1H), 10.02 (d, J=6.6, 1H); ESMS calcd ($C_{18}H_{12}N_2O_2$): 288.1. found: 289.1 (M+H)$^+$.

A solution of 1-acetyl-3-(4-cyanobenzoyl)indolizine (12) (1.56 grams, 5.69 mmol), ethylene glycol (1 mL), and p-toluenesulfonic acid (2.16 grams, 11.38 mmol) in benzene (150 mL) was refluxed for 3 hours. The reaction mixture was cooled to room temperature, neutralized with saturated sodium bicarbonate solution and extracted with ethyl acetate (3×50 mL). The combined layers were concentrated in vacuo. Purification by flash column chromatography ($R_f$ 0.3, ethyl acetate in hexane) afforded 3-(4-cyanobenzoyl)indolizine (13) as a light yellow solid (1.12 grams, 80%). $^1$H NMR (CDCl$_3$) δ 6.56 (d, J=4.8, 1H), 7.04 (t, J=6.9, 1H), 7.28 (m, 2H), 7.61 (d, J=9.0, 1H), 7.78 (m, 2H), 7.89 (m, 2H), 9.98 (d, J=7.2, 1H). ESMS calcd ($C_{16}H_{10}N_2O_2$): 246.1. found: 247.1 (M+H)$^+$.

Sodium cyanoborohydride (0.32 grams, 5.06 mmol) was added in portions to an acetonitrile (15 mL) solution of 3-(4-cyanobenzoyl)indolizine (13) (0.19 grams, 0.84 mmol) and chlorotrimethylsilanen (0.65 mL, 5.06 mmol) cooled in an ice-bath. The reaction mixture was stirred at room temperature for 4 hours. It was then quenched with aqueous sodium bicarbonate solution, extracted with ethyl acetate (3×25 mL). The combined organic layers were washed with water, dried over sodium sulfate and concentrated in vacuo to give an oily residue, which was applied to the flash column chromatography using 10% ethyl acetate in hexane ($R_f$ 0.3) to afford 3-(4-cyanobenzyl)indolizine (14) (0.11 grams, 56% yield). $^1$H NMR (CDCl$_3$) δ 4.09 (s, 2H), 6.36 (m, 2H), 6.56 (m, 2H), 7.15 (d, J=8.4, 2H), 7.32 (d, J=9.3, 1H), 7.45 (m, 3H). ESMS calcd ($C_{16}H_{12}N_2$): 232.1. found: 233.1 (M+H)$^+$.

A solution of oxalyl chloride (1.13 mL, 12.9 mmol) in 40 mL of anhydrous ethyl ether was cooled in an ice-bath, followed by the addition of 3-(4-cyanobenzyl)indolizine (14) (1.04 grams, 4.31 mmol) in ethyl ether (10 mL). The resulting mixture was stirred at 0° C. for 30 minutes. Solvent was removed under reduced pressure (keeping the temperature below 25° C.). The residue was then dissolved in THF (40 mL) and cooled to 0° C. 5-Amino-3-methylisothiazole in THF (10 mL) was added slowly. The mixture was stirred at ambient temperature overnight. The reaction mixture was quenched with water and extracted with ethyl acetate. After concentration in vacuo, the crude product was purified through flash column chromatography with 1:1 ethyl acetate and dichloromethane ($R_f$ 0.3) to give 1.35 grams (78%) of 2-(3-(4-cyanobenzyl)-indolizin-1-yl)-N-(3-methyl-isothiazol-5-yl)-2-oxo-acetamide (1). $^1$H NMR (CDCl$_3$) δ 2.47 (s, 3H), 4.34 (s, 2H), 6.78 (s, 1H), 6.98 (m, 1H), 7.31 (m 3H), 7.61 (d, J=7.2, 2H), 7.80 (d, J=6.9, 1H), 7.85 (s, 1H), 8.68 (d, J=8.7, 1H), 10.36 (s, 1H). ESMS calcd ($C_{22}H_{16}N_4O_2S$): 400.1. found: 399.1 (M−H)$^+$.

Example 2

Preparation of Other 1-Glyoxlylamide Indolizines According to the Method of Scheme 3

The 1-glyoxlylindolizines shown below were prepared using the methods described in Example 1. Analytical data for each compound is provided.

Compound (2)

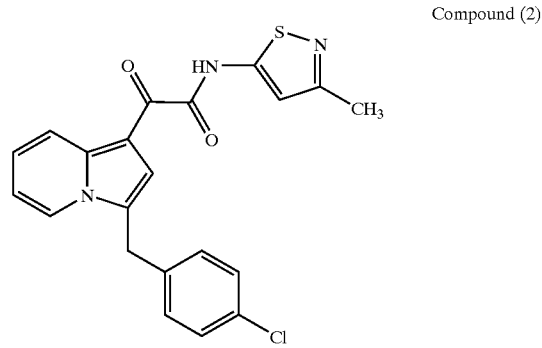

$^1$H NMR (CDCl$_3$) δ 4.22 (s, 2H), 6.78 (s, 1H), 6.95 (m, 1H), 7.13 (d, J=8.1 Hz, 2H), 7.26 (m, 2H), 7.41 (m, 1H), 7.84 (dd, 1H), 8.15 (s, 1H), 8.65 (dd, 1H), 10.21 (s, 1H). ESMS calcd ($C_{21}H_{16}ClN_3O_2S$): 409.1. found: 410.1 (M+H)$^+$.

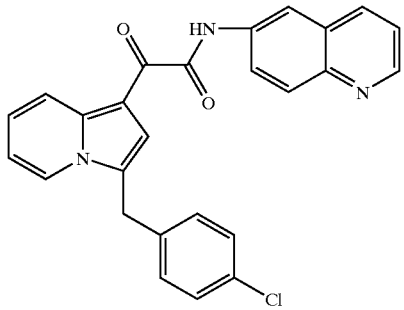

Compound (3)

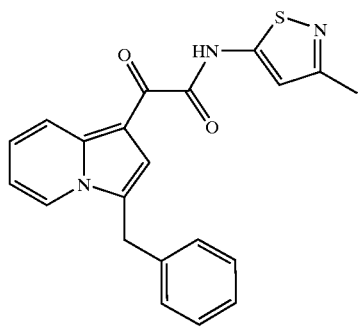

Compound (6)

¹H NMR (CDCl₃) δ 4.22 (s, 2H), 6.92 (m, 1H), 7.50 (m, 5H), 7.84 (m, 2H), 8.13 (m, 2H), 8.57 (s, 1H), 8.67 (d, J=9.0 Hz, 1H), 8.85 (s, 1H), 9.71 (s, 1H). ESMS calcd (C$_{26}$H$_{18}$ClN$_3$O$_2$): 439.1. found: 440.1 (M+H)⁺.

¹H NMR (CDCl₃) δ 2.40 (s, 3H), 4.23 (s, 2H), 6.74 (s, 1H), 6.90 (m, 1H), 7.18–7.41 (m, 6H), 7.81 (m, 1H), 8.16 (s, 1H), 8.62 (m, 1H), 10.22 (s, 1H); ESMS calcd (C$_{21}$H$_{17}$N$_3$O$_2$S): 375. found: 376 (M+H)⁺.

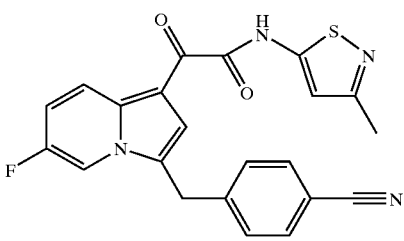

Compound (4)

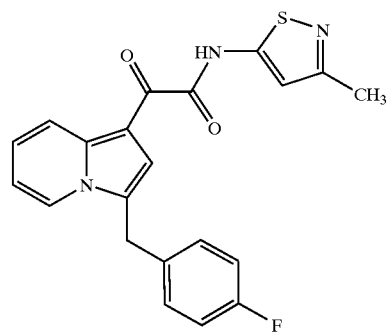

Compound (7)

¹H NMR (CDCl₃) δ 2.50 (s, 3H), 4.30 (s, 2H), 6.81 (s, 1H), 7.2–7.4 (m, 3H), 7.6–7.7 (m, 3H), 8.20 (s, 1H), 8.62 (m, 1H), 10.36 (s, 1H) ppm; ESMS calcd (C$_{22}$H$_{15}$FN$_4$O$_2$S): 418.09. found: 419.1 (M+H)⁺.

¹H NMR (CDCl₃) δ 2.40 (s, 3H), 4.22 (s, 2H), 6.77 (s, 1H), 6.98 (m, 3H), 7.18 (m, 2H), 7.41 (m, 1H), 7.84 (m, 1H), 8.16 (s.1H), 8.62 (m, 1H), 10.20 (s, 1H); ESMS calcd (C$_{21}$H$_{16}$FN$_3$O$_2$S): 393. found: 394 (M+H)⁺.

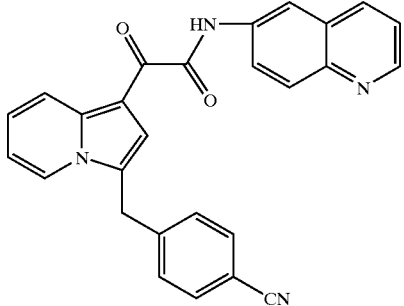

Compound (5)

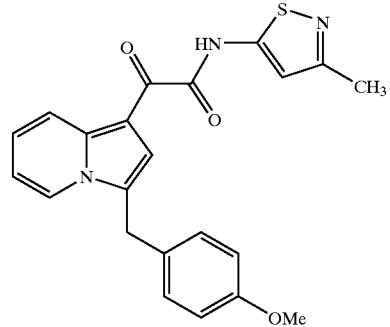

Compound (8)

¹H NMR (CDCl₃) δ 4.34 (s, 2H), 6.96 (m, 1H), 7.42 (m, 4H), 7.75 (m, 3H), 8.17 (m, 2H), 8.42 (d, J=6.9 Hz, 1H), 8.57 (s, 1H), 8.70 (d, J=8.7 Hz, 1H), 8.87 (m, 1H), 9.69 (s, 1H). ESMS calcd (C$_{27}$H$_{18}$N$_4$O$_2$): 430.1. found: 431.1 (M+H)⁺.

¹H NMR (CDCl₃) δ 2.40 (s, 3H), 3.78 (s, 3H), 4.20 (s, 2H), 6.77 (s, 1H), 6.81(m, 2H), 6.92 (m, 1H), 7.13 (m, 2H), 7.40 (m, 1H), 7.87 (m, 1H), 8.14 (s, 1H), 8.62 (m, 1H), 10.46 (s, 1H); ESMS calcd (C$_{22}$H$_{19}$N$_3$O$_3$S): 405. found: 406 (M+H)⁺.

Compound (9)

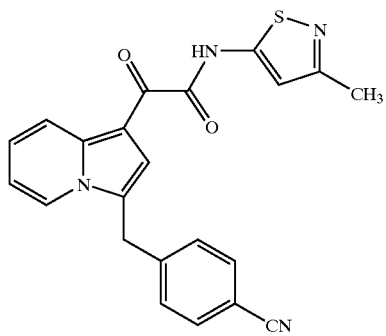

¹H NMR (CDCl₃) δ 2.47 (s, 3H), 4.34 (s, 2H), 6.78 (s, 1H), 6.98 (m, 1H), 7.31 (m 3H), 7.61 (d, J=7.2, 2H), 7.80 (d, J=6.9, 1H), 7.85 (s, 1H), 8.68 (d, J=8.7, 1H), 10.36 (s, 1H). ESMS calcd (C$_{22}$H$_{16}$N$_4$O$_2$S): 400.1. found: 399.1 (M−H)⁺.

Compound (10)

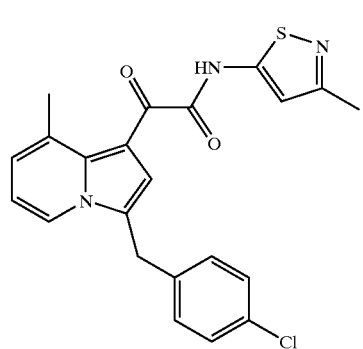

¹H NMR (CDCl₃) δ 2.49 (s, 3H), 2.77 (s, 3H), 4.24 (s, 2H), 6.75 (s, 1H), 6.85 (t, 1H 7.11 (m, 3H), 7.26 (d, 2H), 7.67 (d, 1H), 8.01 (s, 1H), 10.34 (s, 1H); ESMS Calcd (C$_{22}$H$_{18}$ClN$_3$O$_2$S): 423.08. found 424.0 (M+H)⁺.

Compound (11)

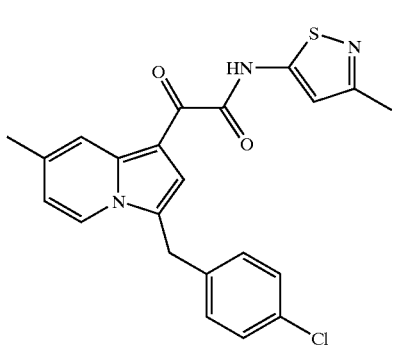

¹H NMR (CDCl₃) δ 2.45 (s, 6H), 4.20 (s, 2H), 6.80 (m, 2H), 7.13 (d, 2H), 7.27 (d, 2H), 7.72 (d, 1H), 8.09 (s, 1H), 8.45 (s, 1H), 10.68 (s, 1H); ESMS Calcd (C$_{22}$H$_{18}$ClN$_3$O$_2$S): 423.08. found 424.0 (M+H)⁺.

Compound (12)

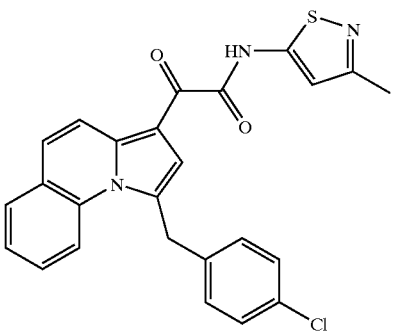

¹H NMR (CDCl₃) δ 2.56 (s, 3H), 4.73 (s, 1H), 6.81 (s, 1H), 7.15 (d, 2H), 7.27 (d, 2H), 7.45 (m, 2H), 7.65 (d, 1H), 7.83 (m, 1H), 8.06 (s, 1H), 8.19 (m, 1H), 8.65 (d, 1H), 10.30 (s, 1H); ESMS Calcd (C$_{25}$H$_{18}$ClN$_3$O$_2$S): 459.08. found 460.0 (M+H)⁺.

Compound (13)

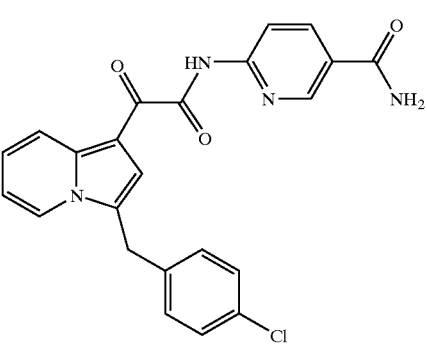

¹H NMR (CDCl₃) δ 4.47 (s, 2H), 7.15 t, 1H), 7.42 (d, 2H), 7.81 (d, 2H), 8.09 (s, 1H), 8.18 (d, 1H), 8.29 (d, 1H), 8.38 (m, 2H), 8.83 (s, 1H), 10.68 (s, 1H)); ESMS Calcd (C$_{23}$H$_{17}$ClN$_4$O$_3$): 432.10. found: 433.1 (M+H)⁺.

Compound (14)

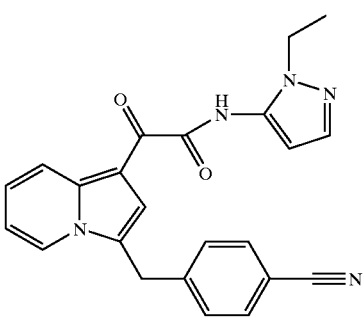

¹H NMR (CDCl₃) δ 1.45 (t, J=7.2 Hz, 3H), 4.18 (q, J=7.2 Hz, 2H), 4.35 (s, 2H), 6.78 (s, 1H), 7.00 (t, J=4.0 Hz, 1H), 7.35 (AB, J-7.8 Hz, 2H), 7.40 (t, J=4.0 Hz, 1H), 7.55 (d, J=1.5 Hz, 1H), 7.62 (AB, J-7.8 Hz, 2H), 7.82 (d, J=5.0 Hz, 1H), 8.15 (s, 1H), 8.65 (d, J=9.1 Hz, 1H), 9.46 (s, 1H) ppm; ESMS calcd (C$_{23}$H$_{19}$N$_5$O$_2$): 397.15. found: 398.1 (M+H)⁺.

Compound (15)

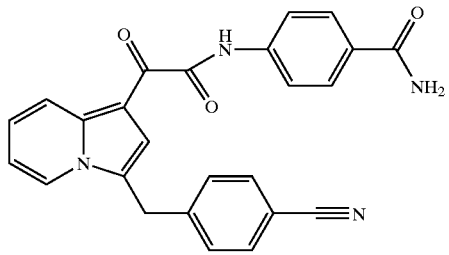

¹H NMR (DMSO-d$_6$) δ 4.45 (s, 2H), 7.15 (m, 1H), 7.55 (m, 3H), 7.8–8.0 (m, 6H), 8.40 (m, 2H), 10.82 (s, 1H) ppm; ESMS calcd (C$_{25}$H$_{18}$N$_4$O$_3$): 422.14. found: 423.2 (M+H)$^+$.

Compound (16)

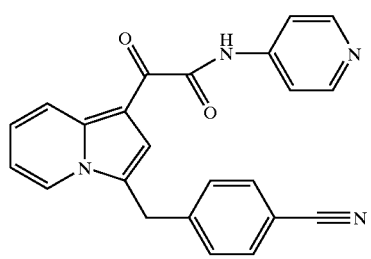

¹H NMR (CDCl$_3$) δ 4.36 (s, 2H), 6.95 (t, J=3.8 Hz, 1H), 7.3–7.5 (m, 3H), 7.6–7.7 (m, 4H), 7.80 (d, J=3.9 Hz, 1H), 8.05 (s, 1H), 8.5–8.7 (m, 3H), 9.60 (s, 1H) ppm; ESMS calcd (C$_{23}$H$_{16}$N$_4$O$_2$): 380.13. found: 381.1 (M+H)$^+$.

Compound (17)

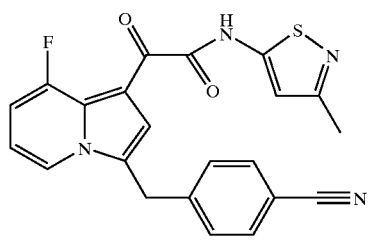

¹H NMR (CDCl$_3$) δ 2.46 (s, 3H), 4.34 (S, 2H), 6.79 (s, 1H), 6.85 (m, 1H), 7.05 (m, 1H), 7.31 (AB, J=8.1 Hz, 2H), 7.6 (m, 3H), 8.14 (s, 11H), 10.42 (s, 1H) ppm; ESMS calcd (C$_{22}$H$_{15}$FN$_4$O$_2$S): 418.09. found: 419.1 (M+H)$^+$.

Compound (18)

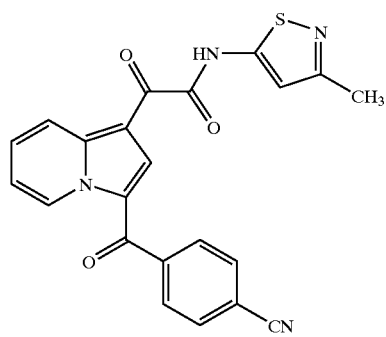

¹H NMR (CDCl$_3$) δ 6.82 (s, 1H), 7.36 (m, 2H), 7.77 (m, 1H), 7.89 (d, J=7.8 Hz, 2H), 7.95 (d, J=9.0 Hz, 2H), 8.77 (d, J=9.6 Hz, 1H), 8.58 (s, 1H), 10.07 (d, J=6.9 Hz, 1H), 10.22 (s, 1H). ESMS calcd (C$_{22}$H$_{14}$N$_4$O$_3$S): 414.1. found: 415.1 (M+H)$^+$.

Compound (19)

¹H NMR (CDCl$_3$) δ 1.26(t, J=7.0 Hz, 3H), 1.45(m, 2H), 2.00(m, 2H), 3.05(t, J=7.2 Hz, 2H), 3.9–4.3(m, 8H), 6.95(t, J=4.3 Hz, 1H), 7.38–7.78(m, 7H), 8.05(s, 1H), 8.62(d, J=8.1 Hz, 1H) ppm; ESMS calcd (C$_{26}$H$_{26}$N$_4$O$_4$): 458.20. found: 459.1 (M+1)+.

Example 3

Preparation of 4-Indolizin-3-yl)-Benzonitrile by the Method Shown in Scheme 1

Scheme 1

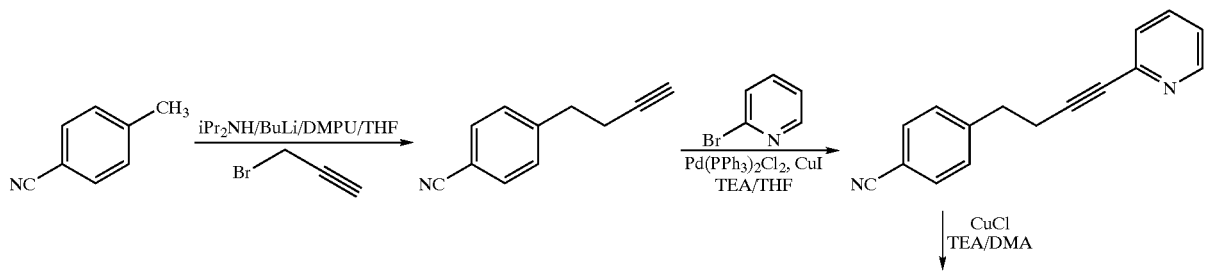

-continued

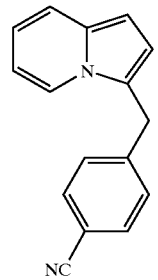

A dried 1 L of three-neck round-bottom flask was flushed with $N_2$, connected to a $N_2$ inlet and equipped with a thermometer. 300 mL of anhydrous THF (Aldrich), 62 mL (0.44 mol) of N,N-diisopropylamine were added to the flask and cooled to −78° C. (30 minutes). n-BuLi (122 mL, 3.6 M, 0.44 mol) was added within 10 minutes, with the internal temperature increasing to −65° C. The resulting mixture was stirred for another 30 minutes at −78° C. DMPU (53 mL, 0.44 mol) was added to the above solution in one portion. The resulting mixture was then stirred at −78° C. for one hour. p-Tolunitrile (48 mL, 0.40 mol) was diluted in 20 mL of THF and added slowly to the above mixture via syringe over 25 minutes, with the temperature below −70° C. The reaction mixture was kept stirring at −78° C. for 40 minutes. The reaction became yellowish red. Propargyl bromide (80%, Aldrich, 22 mL, 0.2 mol) was added over 20 minutes via syringe. The reaction mixture turned light yellow, which was kept stirring at −78° C. for 1.5 h. The reaction was then warmed up to −40° C. 100 mL of saturated $NH_4Cl$ was added, followed by the addition of 100 mL of water. After stirring for 10 minutes at room temperature, 100 mL of ethyl acetate was added and the mixture was transferred to a separatory funnel. The organic layer was separated and the aqueous layer was extracted with 50 mL of ethyl acetate twice. The combined organic layers were washed with water (30 mL) and brine (30 mL), dried over sodium sulfate, and simple filtration gave a clear light yellow solution, which was concentrated in vacuo to give an oil residue, which was cooled to 0° C. A solid formed and was filtered and washed with heptane, which gave 28.64 g (92% yield) of 4-but-3-ynyl-benzontrile. $^1$H NMR ($CDCl_3$): δ (ppm) 7.60 (m, 2H); 7.36 (m, 2H), 2.90 (t, J=7.2 Hz, 2H); 2.51 (m, 2H); 1.99 (t, J=2.7 Hz, 1H). ESMS calcd. ($C_{11}H_9N$): 155.1. found: 156.1 (M+H)$^+$. The obtained product was used for next step without further purification.

A dried 1 L of three-neck round-bottom flask was flushed with $N_2$, connected to a $N_2$ inlet, equipped with a thermometer and a magnetic stirrer. 4-But-3-ynyl-benzonitrile (49.38 g, 0.32 mol) was dissolved in 250 mL of THF, followed by the successive addition of triethylamine (TEA) (250 mL, 1:1 TEA/THF), bromopyridine (33.3 mL, 0.35 mol), Pd (pph$_3$)$_2$Cl$_2$ (4.47 g, 6.0 mmol), and CuI (1.21 g, 6.0 mmol). The reaction mixture was heated up to 65° C. and kept stirring at that temperature. During the heating, it turned dark brown. After 2 h, the reaction was complete and cooled to room temperature, followed by the addition of water (200 mL) and ethyl acetate (200 mL). The organic layer was separated, washed with water (30 mL) and brine (30 mL), and dried over sodium sulfate. After a simple filtration to remove any catalyst residues and drying agents, concentration in vacuo left an oil, which immediately became solid after cooling. The solid was then filtered and washed with heptane to give 58.74 g (79.6% yield; purity: 98%) of 4-(4-pyridin-2-yl-but-3-ynyl)-benzonitrile. $^1$H NMR ($CDCl_3$): δ (ppm) 8.54 (m, 1H); 7.59 (m, 3H); 7.39 (m, 2H); 7.31 (m, 1H); 7.19 (m, 1H); 3.01 (t, J=6.9 Hz, 2H); 2.75 (t, J=6.9 Hz, 2H). ESMS calcd. ($C_{16}H_{12}N_2$): 232.1. found: 233.1 (M+H)$^+$.

A dried 1 L of three-neck round-bottom flask was flushed with $N_2$, connected to a $N_2$ inlet, equipped with a thermometer and a magnetic stirrer. 4-(4-Pyridin-2-yl-but-3-ynyl)-benzonitrile (58.73 g, 0.25 mol), DMA (490 mL) and TEA (70 mL) were successively added to the flask, resulting in a light brown solution. CuCl (25.05 g, 0.25 mol) was then added, after which the reaction turned dark brown. The reaction mixture was kept stirring at 130° C. After stirring for 3 h at 130° C., the reaction was complete, and cooled to room temperature. The reaction was then quenched with water (300 mL), and ethyl acetate (400 mL) was added. The resulting dark brown mixture was then filtered through a celite cake to give a clear two-layer mixture. After separation, drying, and concentration, a dark oil was obtained. The dark oil was dissolved in 250 mL of ethyl acetate, applied to 15 g of decoloring carbon, and stirred for 20 minutes. After filtration through a celite cake, the filtrate was washed with water (100 mL) twice, dried over sodium sulfate. Concentration gave 53.89 g (89%) of 4-indolizin-3-ylmethyl-benzonitrile. $^1$H NMR ($CDCl_3$): δ (ppm) 7.55 (d, J=8.1 Hz, 2H); 7.50 (d, J=9.0 Hz, 1H); 7.39 (d, J=9.0 Hz, 1H); 7.23 (d, J=7.8 Hz, 2H); 6.64 (m, 2H), 6.44 (m, 2H); 4.27 (s, 2H). ESMS calcd. ($C_{16}H_{12}N_2$): 232.1. found: 233.1 (M+H)$^+$.

Example 4

Preparation of other Indolizine Intermediates for the Synthesis of 1-Glyoxlylamide Indolizines by the Method of Scheme 1

The following intermediates were prepared by the method described in Example 3, substituting the appropriate starting materials. Analytical data for each compound is provided.

Intermediate (1)

4-(Indolizin-3-yloxy)-Benzonitrile

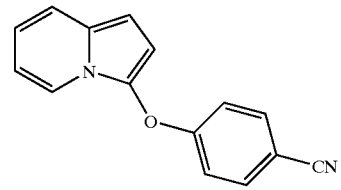

$^1$H NMR ($CDCl_3$): δ (ppm) 7.58 (m, 3H); 7.36 (d, J=9.0 Hz, 1H); 6.99 (m, 2H); 6.64 (m, 1H), 6.51 (m, 3H). ESMS calcd. ($C_{15}H_{10}N_2O$): 234.1. found: 235.1 (M+H)$^+$.

Intermediate (2)

4-(Indolizin-3-yl-Methyl-Amino)-Benzonitrile

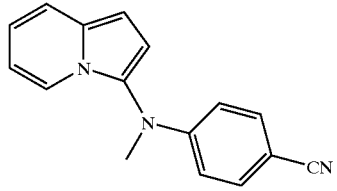

$^1$H NMR (CDCl$_3$): δ (ppm) 7.43 (m, 4H); 6.72 (m, 1H); 6.63 (d, J=3.9 Hz, 1H); 6.49 (m, 4H). ESMS calcd. (C$_{15}$H$_{10}$N$_2$O): 247.1. found: 248.1 (M+H)$^+$.

Intermediate (3)

4-(1-Indolizin-3-yl-Ethyl)-Benzonitrile

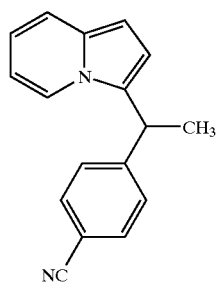

$^1$H-NMR (CDCl$_3$) δ (ppm), 7.55 (d, J=8.7 Hz, 2H), 7.50 (d, J=8.9 Hz, 1H), 7.41 (d, J=8.9 Hz, 1H), 7.24 d, J=8.7 Hz, 2H), 6.65 (m, 2H), 6.45 (m, 2H), 4.43 (q, J=6.7 Hz, 1H), 1.88 (d, J=6.7 Hz, 3H); ESMS clcd for C$_{17}$H$_{14}$: 246.12. Found: 247.1 (M+H)$^+$.

Intermediate (4)

4-(6-Methyl-Indolizin-3-Ylmethyl)-Benzontrile

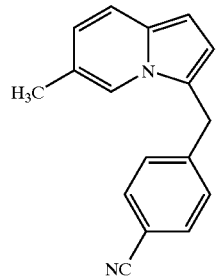

$^1$H-NMR (CDCl$_3$) δ (ppm), 7.58–7.55 (m, 3H), 7.33–7.23 (m, 3H), 6.54–6.50 (m, 2H), 6.39 (d, J=3.9 Hz), 4.25 (s, 2H), 2.17 (s, 3H); ESMS clcd for C$_{17}$H$_4$N$_2$: 246.12. Found: 247.1 (M+H)$^+$.

Intermediate (5)

4-(6-Nitro-Indolizin-3-Ylmethyl)-Benzonitrile

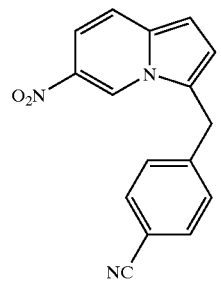

$^1$H-NMR (CDCl$_3$) δ (ppm), 8.92 (d, J=3.6 Hz), 7.76 (d, J=8.7 Hz), 7.56–7.55 (m, 2H), 7.44 (d, J=8.7 Hz, 2H); ESMS clcd for C$_{22}$H$_{15}$N$_5$O$_4$S: 445.08. Found: 446.0 (M+H)$^+$.

Example 5

Preparation of 1-Glyoxlylamide Indolizines from Indolizine Intermediates Prepared by the Method of Example 4

Indolizine intermediates prepared by the method described in Example 4 were converted into 1-glyoxlylamide indolizines by methods described in Example 1. The structures of these 1-glyoxlylamide indolizines and their analytical data are shown below.

Compound (20)

2-[3-(4-Cyano-phenoxy)-indolizin-1-yl]-N-(3-methyl-isothiazol-5-yl)-2-oxo-acetamide

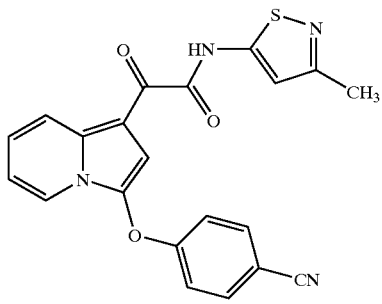

$^1$H NMR (CDCl$_3$): δ (ppm) 10.34 (s, 1H); 8.66 (d, J=9.0, 1H); 8.02 (d, J=6.0, 1H); 7.89 (s, 1H); 7.68 (d, J=9.0, 2H); 7.46 (t, J=9.0, 1H); 7.29 (d, J=9.0, 2H); 7.06 (t, J=6.0, 1H); 6.87 (s, 1H). ESMS calcd (C$_{21}$H$_{14}$N$_4$O$_3$S): 402.1. found: 403.1 (M+H)$^+$.

Compound (21)

2-{3-[(4-Cyano-phenyl)-methyl-amino]-indolizin-1-yl}-N-(3-methyl-isothiazol-5-yl)-2-oxo-acetamide

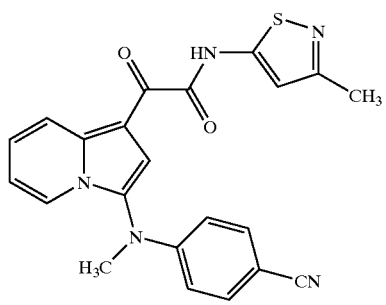

$^1$H NMR (CDCl$_3$): δ (ppm) 10.34 (s, 1H); 8.70 (d, J=9.0, 1H); 8.02 (s, 1H); 7.77 (d, J=6.0, 1H); 7.50 (m, 3H); 7.03 (t, J=9.0, 1H); 6.78 (s, 1H); 6.61 (d, J=9.0, 2H). ESMS calcd (C$_{22}$H$_{17}$N$_5$O$_2$S): 415.1. found: 416.1 (M+H)$^+$.

Compound (22)

2-{3-[1-(4-Cyano-phenyl)-ethyl]-indolizin-1-yl}-N-(3-methyl-isothiazol-5-yl)-2-oxo-acetamide

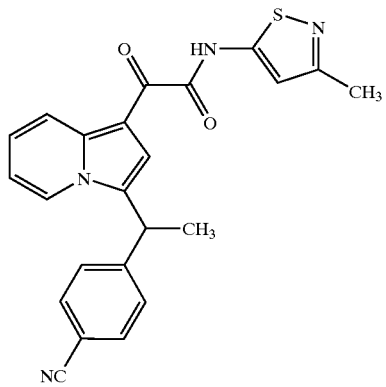

$^1$H-NMR (CDCl$_3$) δ (ppm), 10.52 (s, 1H), 8.65 (d, J=9.9 Hz, 1H), 8.35 (s, 1H), 7.66 (d, J=6.6 Hz, 1H), 7.59 (d, J=8.7 Hz, 2H), 7.39 (dd, J$_1$=9.9 Hz, J$_2$=7.5 Hz, 1H), 7.28 (d, J=8.7 Hz, 2H), 6.89 (dd, J$_1$=6.6 Hz, J$_2$=7.5 Hz, 1H), 6.81 (s, 1H), 4.33 (q, J=6.9 Hz, 1H), 2.46 (s, 3H), 1.83 (d, J=6.9 Hz, 3H); ESMS clcd for C$_{23}$H$_{18}$N$_4$O$_2$S: 414.12. Found: 415.1 (M+H)$^+$.

Compound (23)

2-[3-(4-cyano-benzyl)-6-hydroxy-indolizin-1-yl]-N-(3-methyl-isothiazol-5-yl)-2-oxo-acetamide

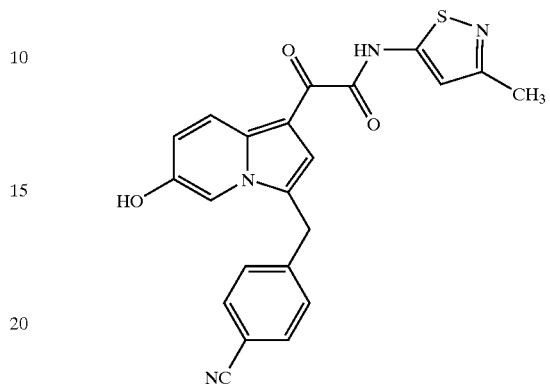

$^1$H-NMR (DMSO-d$_6$) δ (ppm), 10.06(s, 1H), 8.37(d, J=9.0 Hz, 1H), 7.82–7.76(m, 3H), 7.63(s, 1H), 7.48–7.45(m, 2H), 7.26–7.23(m, 1H), 7.01(s, 1H), 4.39(s, 2H), 2.34(s, 3H); ESMS clcd for C$_{22}$H$_{16}$N$_4$O$_3$S: 416.09. Found: 417.0 (M+H)$^+$.

Compound (24)

2-[3-(4-Cyano-benzyl)-6-methyl-indolizin-1-yl]-N-(3-methyl-isothiazol-5-yl)-2-oxo-acetamide

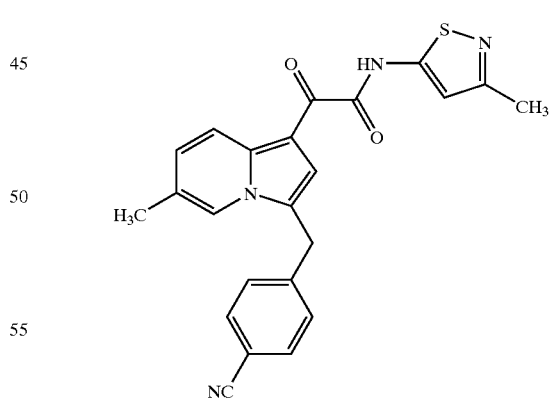

$^1$H-NMR (DMSO-d$_6$) δ (ppm), 8.40 (d, J=8.7 Hz, 1H), 8.31 (s, 1H), 7.54 (d, J=8.1 Hz, 2H), 7.60 (s, 1H), 7.52 (d, J=8.1 Hz, 2H), 7.43 (d, J=8.7 Hz, 1H), 7.02 (s, 1H), 4.43 (s, 2H), 2.35 (s, 3H), 2.34 (s, 3H); ESMS clcd for C$_{23}$H$_{18}$N$_4$O$_2$S: 414.12. Found: 415.1 (M+H)$^+$.

Compound (25)

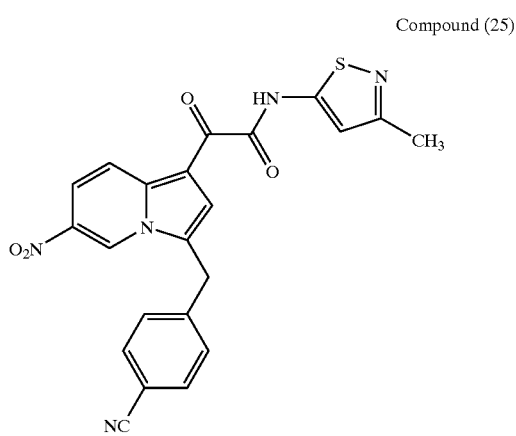

2-[3-(4-Cyano-benzyl)-6-nitro-indolizin-1-yl]-N-(3-methyl-isothiazol-5-yl)-2-oxo-acetamide $^{1}$H-NMR (DMSO-d$_{6}$) δ (ppm), 9.42 (d, J=1.2 Hz), 8.53 (d, J=9.9 Hz), 8.13 (dd, J$_{1}$9.9 Hz, J$_{1}$=1.2 Hz), 7.84 (d, J$_{1}$=8.4 Hz, 2H), 7.81 (s, 1H), 7.55 (d, J$_{1}$=8.4 Hz, 1H), 7.04 (s, 1H), 4.64 (s, 1H), 2.35 (s, 3H); ESMS clcd for C$_{22}$H$_{15}$N$_{5}$O$_{4}$S: 445.08. Found: 446.0 (M+H)$^{+}$.

Example 6

Preparation of 4-Indolizin-3-yl)-Benzonitrile by the Method Shown in Scheme 2

To 4-acetylbenzonitrile (14.5 g, 100 mmol) EtOAc (150 ml) solution was added Br$_{2}$ (5.1 ml, 100 mmol) at room temperature. The resulting mixture was stirred for 0.5 hr, and the solvent was evaporated under reduced pressure. The residue was dissolved in CH$_{3}$CN (100 ml), and picoline (20 ml, 200 mmol) was added to the mixture, which was then stirred for 30 minutes at room temperature and another 1 hr at 0° C. EtOAc (20 ml) was added to the mixture and the resulting precipitate was collected by filtration and washed with EtOAc to give pure 2-methyl-1-(4-cyno)-phenacylpyridinium bromide (20.3 g, 83%). $^{1}$H NMR (300 MHz, DMSO): 9.05–8.03(m, 8H), 6.78(s, 2H), 2.74(s, 3H).

A 400 ml mixture of DMF-Me$_{2}$SO$_{4}$ reagent was obtained by stirring a mixture of 1 eq DMF and 1 eq Me$_{2}$SO$_{4}$ at 60° C. for 3 h and then cooled to room temperature. This reagent was added to a 2-methyl-1-(4-cyno)-phenacylpyridinium bromide (50 g, 120 mmol) DMF (500 ml) suspension solution. The resulting mixture was stirred at room temperature for 15 minutes. Et$_{3}$N (700 ml) was then added to the mixture, which was and stirred for 1 hr while maintaining the temperature at 40° C. To the resulting mixture was added ice water (1200 ml). The resulting precipitate was collected, washed with water, and dried, to give 4-(indolizine-3-carbonyl)-benzonitrile (29 g, yield 76%). $^{1}$H NMR (300 MHz, CDCl$_{3}$): 9.95 (d, 1H), 7.87–7.75(m, 4H), 7.57(d, 1H), 7.30–7.22(m, 2H), 6.97(m, 1H), 6.55(d, 1H); ESMS clcd for C$_{16}$H$_{10}$N$_{2}$O: 246.08. Found: 247.1 (M+H)$^{+}$.

In an alternative procedure, 4-(indolizine-3-carbonyl)-benzonitrile was prepared by adding N,N-dimethylformamide di-t-butyl acetal (30 ml) to a suspension of 2-methyl-1-(4-cyno)-phenacylpyridinium bromide (5 g, 12.2 mmol) in DMF (50 ml) at room temperature. The clear solution was stirred at 130° C. for 4 minutes and cooled to room temperature with an ice-water bath. Water (100 ml) was added, the precipitate was collected, washed with water and dried with vacuum line to give 4-(indolizine-3-carbonyl)-benzonitrile (3.9 g, 90%) with 91% purity. This product was crystallized with CH$_{3}$CN(35 ml) (82° C. to 0° C.) to give pure 2 (3.2 g). $^{1}$H NMR (300 MHz, CDCl$_{3}$): 9.95 (d, 1H), 7.87–7.75(m, 4H), 7.57(d, 1H), 7.30–7.22(m, 2H), 6.97(m, 1H), 6.55(d, 1H); ESMS clcd for C$_{16}$H$_{10}$N$_{2}$O: 246.08. Found: 247.1 (M+H)$^{+}$.

To 4-(indolizine-3-carbonyl)-benzonitrile (24 g, 100 mmol) CH$_{3}$CN (600 ml) solution containing MeOH (9 ml) was added BH$_{3}$-THF (1M, 480 ml). The resulting mixture was stirred at 50° C. for 1 hr. The reaction was quenched with water (200 ml), and extracted with EtOAc (700 ml), and washed with water (300 ml×3). The organic layer was evaporated under reduced pressure, and the residue was dissolved in ether (or EtOAc) (400 ml), diluted with hexanes (100 ml) and filtered with celite to give 4-indolizin-3-ylmethyl-benzonitrile (15.6 g, 92% purity by HPLC). This product was used directly for the next step. δ (ppm) 8.54 (m, 1H); 7.59 (m, 3H); 7.39 (m, 2H); 7.31 (m, 1H); 7.19 (m, 1H); 3.01 (t, J=6.9 Hz, 2H); 2.75 (t, J=6.9 Hz, 2H). ESMS calcd. (C$_{16}$H$_{12}$N$_{2}$): 232.1. found: 233.1 (M+H)$^{+}$.

Example 7

Preparation of other Indolizine Intermediates for the Synthesis of 1-Glyoxlylamide Indolizines by the Method of Scheme 2

The indolizine intermediates shown below were prepared by the method described in Example 6. Analytical data is provided for each compound.

Intermediate (6)

4-(6-Hydroxy-indolizine-3-carbonyl)-benzonitrile $^{1}$H-NMR (DMSO-d$_{6}$) δ (ppm), 9.94(s, 1H), 9.64(s, 1H), 8.00–7.98(m, 2H), 7.88–7.84(m, 2H), 7.73–7.69(m, 1H), 7.15–7.11(m, 2H), 6.61(d, J=4.8 Hz, 1H); ESMS clcd for C$_{16}$H$_{10}$N$_{2}$O$_{2}$: 262.07. Found: 263.1 (M+H)$^{+}$.

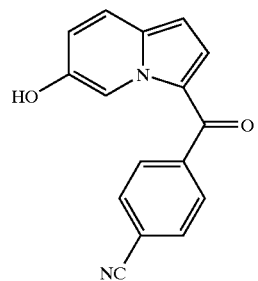

Intermediate (7)

Furan-2-yl-indolizin-3-yl-methanone

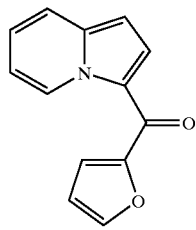

¹H-NMR (CDCl₃) δ (ppm), 10.01(d, J=7.2 Hz, 1H), 8.05(d, J=4.5 Hz, 1H), 7.63(s, 1H), 7.56(d, J=8.7 Hz, 1H), 7.29–7.27 m, 1H), 7.17(t, J=6.9 Hz, 1H), 6.91(t, J=6.9 Hz, 1H), 6.60–6.56(m, 2H); ESMS clcd for $C_{13}H_9NO_2$: 211.06. Found: 212.1 (M+H)⁻.

Intermediate (8)

5-(Indolizine-3-carbonyl)-thiophene-2-carbonitrile

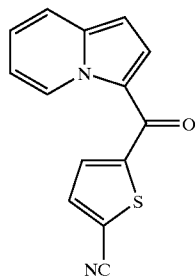

¹H-NMR (CDCl₃) δ (ppm), 9.88(d, J=6.9 Hz, 1H), 7.68–7.63(m, 4H), 7.30–7.25(m, 1H), 7.00(t, J=6.9 Hz, 1H), 6.61(d, J=4.5 Hz, 1H); ESMS clcd for $C_{14}H_8N_2OS$: 252.04; Found: 253.0 (M+H)⁺.

Intermediate (9)

5-Indolizin-3-ylmethyl-thiophene-2-carbonitrile

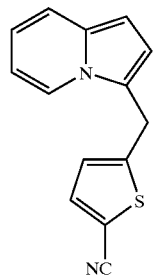

¹H-NMR (CDCl₃) δ (ppm), 7.59(d, J=7.2 Hz, 1H), 7.46–7.40(m, 2H), 6.80–6.78(m, 1H), 6.72–6.66(m, 2H), 6.51(t, J=6.6 Hz, 1H), 6.46(d, J=3.9 Hz, 1H), 4.46(s, 2H); ESMS clcd for $C_{14}H_{10}N_2S$: 238.05. Found: 239.1 (M+H)⁺.

Example 8

Preparation of 1-Glyoxylamide Indolizines from Indolizine Intermediates Prepared by the Method of Example 6

Indolizine intermediates prepared by the method described in Example 6 were then converted into 1-glyoxylamide indolizines by methods described in Example 1. The structures of these 1-glyoxylamideindolizines and their analytical data are shown below.

Compound (26)

2-[3-(3-Cyano-benzyl)-indolizin-1-yl]-N-(3-methyl-isothiazol-5-yl)-2-oxo-acetamide

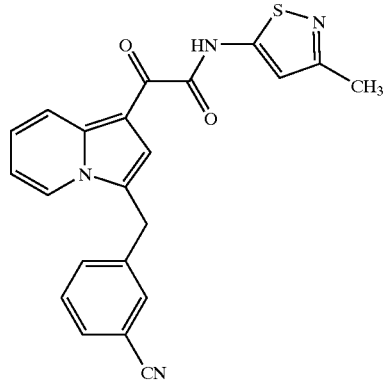

¹H-NMR (CDCl₃) δ (ppm), 10.43 (s, 1H), 8.67(d, J=9.0 Hz, 1H), 8.17(s, 1H), 7.82(d, J=6.9 Hz, 1H), 7.59–7.40(m, 4H), 6.99(t, J=6.6 Hz, 1H), 6.78(s, 1H), 4.30(s, 2H), 2.46(s, 3H); ESMS clcd for $C_{22}H_{16}N_4O_2S$: 400.10. Found: 401.0 (M+H)⁻.

Compound (27)

2-[3-(5-chloro-thiophen-2-ylmethyl)-indolizin-1-yl]-N-(3-methyl-isothiazol-5-yl)-2-oxo-acetamide

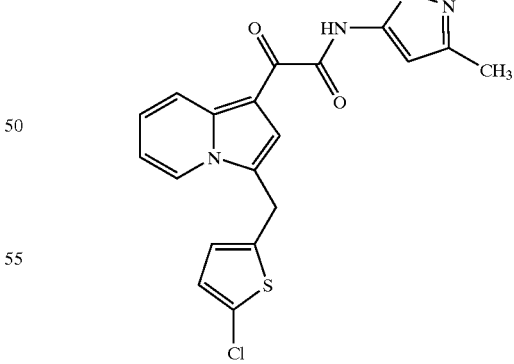

¹H-NMR (CDCl₃) δ (ppm), 10.52(s, 1H), 8.64(d, J=9.0 Hz, 1H), 8.19(s, 1H), 7.95(d, J=6.9 Hz, 1H), 7.42(t, J=7.2 Hz, 1H), 7.00(t, J=6.9 Hz, 1H), 6.78(s, 1H), 6.74–6.73(m, 1H), 6.62–6.61(m, 1H), 4.35(s, 2H), 2.45(s, 3H); ESMS clcd for $C_{19}H_{14}ClN_3O_2S_2$: 415.02. Found: 416.0 (M+H)⁺.

Compound (28)

2-[3-(5-cyano-thiophen-2-ylmethyl)-indolizin-1-yl]-N-(3-methyl-isothiazol-5-yl)-2-oxo-acetamide

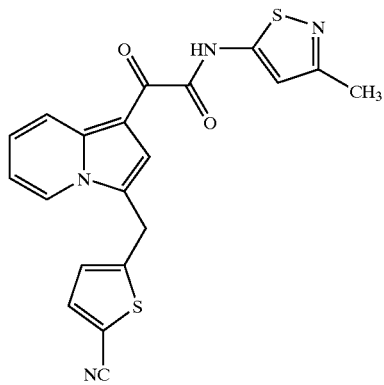

$^1$H-NMR (CDCl$_3$) δ (ppm), 10.40(s, 1H), 8.66(d, J=9.0 Hz, 1H), 8.24(s, 1H), 7.88(d, J=6.9 Hz, 1H), 7.49–7.42(m, 2H), 7.03(t, J=6.0 Hz, 1H), 6.88(d, J=3.9 Hz, 1H), 6.79(s, 1H), 4.48(s, 2H), 2.46(s, 3H); ESMS clcd for C$_{20}$H$_{14}$N$_4$O$_2$S$_2$: 406.06. Found: 407.0 (M+H)$^+$.

Example 9

Compound (1) Demonstrates Anti-Cancer Activity (In Vitro)

The in vitro activity of the compounds was determined in the following seven human cancer cell lines. MDA435 (human breast cancer), MIP101 (human colon cancer), HL-60 (human myeloid leukemia), U937 (human leukemia), p388 (murine leukemia), DU-145 (human prostate cancer), MES-SA (human uterine sarcoma) were obtained from ATCC (American Type of Culture Collection).

The cell lines were maintained in RPMI1640(GIBCO) supplemented with 10% FCS, 100 units/ml penicillin, 100 ug/ml streptomycin, and 2 mM L-glutamine. The cells were split every third day and diluted to a concentration of 2×10$^5$ cells/ml one day before experiment. All experiments were performed on exponentially growing cell culture. Cell densities were 2.5×10$^4$ cells/ml in all experiment.

A stock solution of Compound (1) and a stock solution of Taxol (positive control) were prepared by dissolving the compound at a concentration of 1 mM in 100% DMSO. Final concentrations were obtained by diluting the stock solution directly into the tissue culture medium. Cells were incubated with varying concentrations of the compounds for 72 hours and the IC$_{50}$ was determined by MTS (i.e. 3-(4.5.-dimethylthiazol-2-yl)-2.5-diphenyl tetrazolium bromide) assay. IC$_{50}$ stands for the concentration of compound required to inhibit 50% tumor cell growth. The results are shown in Table 1.

TABLE 1

In Vitro Anti-Cancer Activity of Compound (1) and Taxol (positive control)

| Cancer Cell Lines | IC$_{50}$ (uM) | |
|---|---|---|
| | Compound (1) | Taxol |
| MDA-435 | 0.05 | 0.005 |
| MIP-101 | 0.02 | 0.5 |
| HL-60 | 0.01 | 0.005 |
| U-937 | 0.05 | 0.005 |
| p388 | 0.01 | 0.01 |
| DU-145 | 0.05 | 0.005 |
| MES-SA | 0.01 | 0.005 |

As can be seen from the data in Table 1, Compound (1) demonstrated significantly high anti-cancer activity (IC$_{50}$: 0.01~0.05 uM) against seven cancer cell lines from different tissue types.

Example 10

Compound (1) has Anti-Cancer Activity against Multi-Drug Resistant Cancer Cells In Vitro In vitro activity was determined in two MDR (Multi Drug Resistant) human cancer cell lines. HL-60/TX1000 was isolated in vitro by subculturing HL-60 in progressively higher concentration of Taxol. HL-60/TX1000 cells over-express mdr-1 mRNA and p-glycoprotein, as determined by western blot and immunofluorescence labeling with antiPGP antibodies. The cell is cross-resistant to Taxol, Vincristine, Adriamycin, Etoposide and Doxorubicin. MES-SA/Dx5 was established in the presence of increasing concentrations of Doxorubicin. The cells express high levels of mdr-1 mRNA and p-glycoprotein and exhibit cross resistance to more than fifteen chemotherapeutic agents including Taxol, Etoposide, Mitomycin C, Colchicine, Vinblastine, Dactinomycin, 5-Fluorouracil and Methotrexate. MES-SA/Dx5 was purchased from ATCC.

The procedure for culturing the cells and assaying cancer cell growth inhibition were as described in Example 3. The results are shown in Table 2.

TABLE 2

In Vitro Anti-Cancer Activity of Compound (1), Taxol (control) and Vincristine (control) Against Multi Drug Resistance Cancer Cell Lines

| Cell Lines | IC$_{50}$ (uM) | | |
|---|---|---|---|
| | Compound (1) | Taxol | Vincristine |
| HL-60/TX1000 | 0.02 | 5 | 5 |
| MES-SA/DX-5 | 0.05 | 5 | 1 |

Taxol and Vincristine were not effective (IC$_{50}$: 1–5 uM) against the MDR cell lines (MES-SA/DX5, HL-60/TX1000). On the other hand, Compound (1) showed high anti-cancer activity against these MDR cancer cell lines.

Example 11

Compound (1) Demonstrates Anti-Cancer Efficacy on Human Breast Tumor (MDA435) Xenograft Model (In Vivo)

The in vivo anti-cancer efficacy of Compound (1) was assessed in tumor bearing mice using a tumor growth inhibition assay. Human breast tumor (MDA-435) cells were implanted by injection of a tumor cell suspension subcutaneously in the flank of a nude mouse. Treatment of the tumor with an experimental compound began after the tumor had been established (volume was approximately 100 mm$^3$). The animal then began a multiple injection schedule where the compound was administered orally. Tumors were measured two times a week. During the course of this assay, animals were monitored daily for signs of toxicity including body weight loss.

A supplemented media was prepared from 50% DMEM/Dulbecco Modified Eagle Medium (High Glucose), 50% RPMI 1640, 10% FBS/Fetal Bovine Serum (Hybridoma Tested; Sterile Filtered), 1% L-Glutamine, 1% Penicillin-Streptomycin, 1% MEM Sodium Pyruvate, 1% MEM Non-Essential Amino Acids. FBS was obtained from Sigma Chemical Co. and other ingredients were obtained from Invitrogen Life Technologies, USA). The supplemental media was warmed to 37° C. and 50 ml of media was added to a 175 cm$^2$ tissue culture flask.

The cells used in the assay were MDA435 Human Breast Carcinoma from the American Type Culture Collection. One vial of MDA-435 cells from the liquid nitrogen frozen cell stock was removed. The frozen vial of cells was immediately placed into a 37° C. water bath and gently swirled until thawed. The freeze-vial was wiped with 70% ethanol and cells were immediately pipetted into the 175 cm$^2$ tissue culture flask containing supplemented media. The cells were incubated overnight and the media was removed and replaced with fresh supplemented media the next day. The flask was incubated until the flask became about 90% confluent. This typically took about 5–7 days.

The flask was washed with 10 ml of sterile room temperature phosphate buffered saline (PBS). The cells were trypsinized by adding 5 ml of warmed Trypsin-EDTA (Invitrogen) to the flask of cells. The cells were then incubated for 2–3 minutes at 37° C. until cells begun to detach from the surface of the flask. An equal volume of supplemented media (5 ml) was added to the flask. All the cells were collected into 50 ml tube, and centrifuged at 1000 RPM for 5 minutes at 20° C. The supernatant was aspirated and the cell pellet was resuspended in 10 ml of supplemented media and the cells were counted. 1–3 million cells/flask were seeded into 5–7 tissue culture flasks (175 cm$^2$). Each flask contained 50 ml of supplemented media. The flasks were incubated until about 90% confluent. The passaging of the cells was repeated until enough cells have been grown for tumor implantation.

The above procedure for trypsinizing and centrifuging the cells were followed. The supernatant was aspirated and the cell pellet was resuspended in 10 ml of sterile PBS and the cells were counted. The cells were centrifuged and then resuspended with appropriate volume of sterile PBS for injection of correct number of cells needed for tumor implantation. In the case of MDA-435, 100 million cells were suspended with 2.0 ml of sterile PBS to a final concentration of 50 million cells/ml in order to inject 5 million cells in 0.1 ml/mouse.

Mice (CD-1 nu/nu) were obtained from Charles River Laboratories: nomenclature: Crl:CD-1-nuBR, Age: 6–8 weeks. The mice were allowed to acclimate for 1 week prior to their being used in an experimental procedure.

Implantation of the MDA-435 tumor cell suspension took place into the corpus adiposum of the female CD-1 nu/nu mouse. This fat body is located in the ventral abdominal viscera of the mouse. Tumor cells were implanted subsutaneously into the fat body located in the right quadrant of the abdomen at the juncture of the os coxae (pelvic bone) and the os femoris (femur). 5 million MDA-435 cells in 0.1 ml of sterile PBS were injected using 27 G (½ inch) needle. MDA-435 tumors developed 2–3 weeks after implantation.

A dosing solution for compound administration was prepared by dissolving 1 gram of Compound (1) in 10 ml of acetone (HPLC grade), and sonicated for 5 minutes using 550 Sonic Dismembrator. 1.2 equivalents of 1 N HCl aqueous solution were added to the acetone solution which was then sonicated for 5 minutes. All solvent was then evaporated from the solution by using Speed Vac Plus SC 250 DDA over night. The dried powder was used for preparing the dosing solution of Compound (1). 1% Methyl cellulose (MC) vehicle was prepared by dissolving 1.0 gram of Methyl cellulose, 400 cps, U.S.P. (Spectrum Laboratory Products, Cat. # ME136) in 100 mL of H$_2$O. This mixture was then stirred for 12 hours at room temperature to produce a clear 1% MC solution. After autoclaving the solution for 15 minutes at 120° C., the 1% MC solution was allowed to stand at room temperature for 3 hours prior to being used for formulating orally administered compounds. Compound (1) was prepared in 1% MC and orally administered to the mice through a standard gavage tube attached to a hypodermic syringe. This method permits a direct placement of the compound into the stomach. The dosing volume for the mice was 10 mL/kg.

1% MC Dosing Solution of the Compound (1) was injected orally into the mice bearing MDA435 human breast tumor according to the following protocol:

| Group | Compounds | Dose |
| --- | --- | --- |
| 1 | Vehicle | |
| 2 | Compound (1) | 25 mg/kg |
| 3 | Compound (1) | 50 mg/kg |

Dosing schedule: 3 times a week (Monday, Wednesday, Friday) for 3 weeks; 5 mice were used for each group FIG. 1 shows the anti-tumor efficacy of Compound (1). As can be seen from FIG. 1, Compound (1) significantly inhibits tumor growth of MDA435 in nude mice at 25 mg/kg and 50 mg/kg in a dose dependent manner. FIG. 2 shows the effects of Compound (1) on the body weight of nude mice bearing MDA435 human breast tumor. As can be seen from FIG. 2, Compound (1) demonstrates anti-cancer activity without showing significant body weight loss of mice.

Example 12

Compounds (2)–(8) Demonstrates High Anti-Cancer Activity against MES-SA/DX5 (In Vitro)

The protocol described in Examples 9–10 was used to assay inhibition by Compounds (2)–(8) on the growth of the multidrug resistant cancer cell line MES-SA/DX5, which is a MDR uterine sarcoma cell line. The results are shown in Table 3.

TABLE 3

In Vitro Anti-Cancer Activity of Compound (2)–(8) against Multi Drug Resistance Human Uterine Sarcoma Cell Lines, MES-SA/DX5

| Compound | IC$_{50}$ (uM) |
| --- | --- |
| Compound (2) | 0.06 |
| Compound (3) | 0.1 |
| Compound (4) | 0.05 |

TABLE 3-continued

In Vitro Anti-Cancer Activity of Compound (2)–(8) against Multi Drug Resistance Human Uterine Sarcoma Cell Lines, MES-SA/DX5

| Compound | IC$_{50}$ (uM) |
| --- | --- |
| Compound (5) | 0.1 |
| Compound (6) | 0.05 |
| Compound (7) | 0.05 |
| Compound (8) | 0.1 |

Compounds (2)–(8) demonstrated significant anti-cancer activity (IC$_{50}$: 0.05–0.1 uM) against MES-SA/DX5, while Taxol showed weak anti-cancer activity (IC50: 5 uM) against the MDR cell line.

Example 13

Compounds (20) (21) (24) and (28) Demonstrates High Anti-Cancer Activity against MES-SA and DU-145 (In Vitro)

The protocol described in Examples 9–10 was used to assay inhibition by Compounds (20) (21) (24) and (28) on the growth of cancer cell lines MES-SA (human uterine sarcoma cell line) and DU-145 (human prostate cancer). The results are shown in Table 4.

TABLE 4

In Vitro Anti-Cancer Activity of Compound (20) (21) (24) (28) against MES-SA and DU-145

| Compound | IC$_{50}$ (uM) MES-SA | IC$_{50}$ (uM) DU-145 |
| --- | --- | --- |
| Compound (20) | 0.05 | 0.05 |
| Compound (21) | 0.05 | 0.05 |
| Compound (24) | 0.05 | 0.05 |
| Compound (28) | 0.1 | 0.1 |

Compounds (20), (21), (24) and (28) demonstrated significant anti-cancer activity (IC$_{50}$: 0.05–0.1 uM) against MES-SA and DU-145.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by the following structural formula:

or a pharmaceutically acceptable salt thereof, wherein:

Ring A is substituted or unsubstituted and is optionally fused to an aryl group;

$Z_1$ and $Z_2$ are independently =O, =S, =N—OR$_{12}$ or =NR$_{12}$;

$R_1$ and $R_2$ are independently —H, an aliphatic group, a substituted aliphatic group, or a substituted or unsubstituted aryl group selected from:

provided that $R_1$ and $R_2$ are not both —H;

$R_3$ is a substituted or unsubstituted aliphatic group or a substituted or unsubstituted aryl group represented by Ring V:

wherein Z is —O—, —S—, —NR—, or —CH=CH— and R is —H or C1–C4 alkyl;

X is a covalent bond, —C(R$_4$R$_5$)—, —N(R$_4$)—, —O—, —S—, —S(O)—, —S(O)$_2$—, —C(=O)—, —C(=O)—N(R$_4$)—, or —N(R$_4$)—C(=O)—, $R_4$ and $R_5$ are independently —H or a substituted or unsubstituted aliphatic group; and $R_{12}$ is —H or a substituted or unsubstituted alkyl group.

2. The compound of claim 1 wherein: Ring A is substituted or unsubstituted; $Z_1$ and $Z_2$ are both =O; $R_1$ is —H; $R_3$ is a substituted or unsubstituted alkyl or aryl group; $R_1$ is a substituted or unsubstituted aryl group; and X is —C(R$_4$R$_5$)—, —N(R$_4$)— or —O—.

3. The compound of claim 2 wherein Rings D, E, M, and N are independently unsubstituted or substituted with a group independently selected from —OH, —Br, —Cl, —I, —F, —OR$^a$, —O—COR$^a$, —COR$^a$, —CN, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NRCOR$^a$, —NHCONH$_2$, —NCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$_c$)—NHR$^a$, —NH—C(=NR$^c$)—N(R$^a$R$^b$), —NR$^d$H—C(=NH)—NH$_2$, —NR$^d$—C(=NH)—NHR$^a$, —NR$^d$—C(=NH)—N(R$^a$R$^b$), —NR$^d$—C(=NR$^c$)—NH$_2$, —NR$^d$—C(=NR$^c$)—NHR$^a$, —NR$^d$—C(=NR$^c$)—N(R$^a$R$^b$), —NHNH$_2$, —NHNHR$_a$, —NH$^a$R$^b$, —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SR$^a$, —S(O)R$^a$, —S(O$_2$R$^a$, alkyl groups, substituted alkyl group, benzyl group, substituted benzyl group, aryl group and substituted aryl group; wherein R$^a$—R$^d$ are each independently an alkyl group, substituted alkyl group, benzyl, substituted benzyl, aryl or substituted aryl group.

4. The compound of claim 2 wherein Rings D, E, M, and N are independently unsubstituted or substituted with a group selected from C1–C4 alkyl, C1–C4 hydroxyalkyl, —N(C1–C4 alkyl)$_2$, —C(O)NH$_2$, —C(O)NH(C1–C4 alkyl), C(O)N(C1–C4 alkyl)$_2$, —NHC(O)(C1–C4 alkyl), —NO$_2$, C1–C4 alkoxy, —C(O)O—CH$_2$CH$_2$—N(C1–C4 alkyl)$_2$,

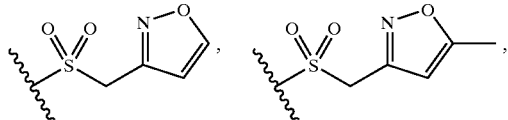

—NN-(phenyl), —NH$_2$, —CH$_2$NH—C(O)—O—(C1–C4 alkyl), —CH$_2$NH$_2$, —Cl, —F, —C(O)—O—(C1–C4 alkyl), —C(O)—N—(C1C4 alkyl), C3–C7 cycloalkyl, phenyl, S—(C1–C4 alkyl), —CN, furyl, —S(O)$_2$—(C1–C4 alkyl), —S(O)$_2$—NH$_2$, —S(O)$_2$—NH(C1–C4 alkyl), and —S(O)$_2$—N(C1–C4 alkyl)$_2$.

5. The compound of claim 4 wherein R$_2$ is represented by a structural formula selected from:

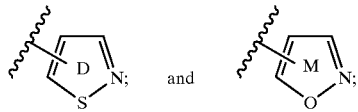

and R$_6$ is —H or a substituted or unsubstituted alkyl group.

6. The compound of claim 4 wherein R$_2$ is represented by a structural formula selected from:

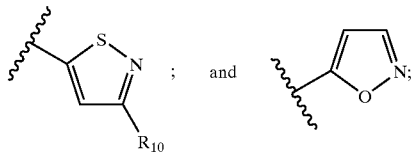

wherein:
R$_{10}$ is —H or an alkyl group.

7. The compound of claim 6 wherein Ring A is optionally substituted with one or more groups selected from —F, —Cl, —Br, —C1–C4 alkyl, C1–C4 alkoxy, —C1–C4 haloalkyl, C1–C4 haloalkoxy, —NH$_2$ and —CN.

8. The compound of claim 7 wherein:
Ring A is unsubstituted;
R$_3$ is a phenyl group that is unsubstituted or substituted with one or more substituents selected from —Br, —Cl, —F, —R$^e$, —OR$^e$, —CN, —COOR$^e$, —N(R$^e$)$_2$—CON(R$^e$), —NR$^e$COR$^f$, —NHCONH$_2$, —SO$_2$, and N(R$^e$)$_2$; and
each R$^e$ and R$^f$ are independently —H, an alkyl group or a substituted alkyl group.

9. The compound of claim 8 wherein R$_3$ is a phenyl ring that is unsubstituted or substituted with one or more substituents selected from —Cl, —F, —R$^e$, —OR$^e$, —CN, —NH$_2$, —CONH$_2$ and —NHCOR$^f$.

10. The compound of claim 9 wherein R$_3$ is a phenyl ring that is unsubstituted or substituted with one or more substituents selected from —CH$_3$, —CH$_2$CH$_3$, —OCH$_3$, —CN, —F and —Cl.

11. The compound of claim 10 wherein R$_3$ is a phenyl ring that is unsubstituted or monosubstituted wit —CH$_2$CH$_3$, —OCH$_3$, —CN, —F or —Cl$_3$ and wherein the phenyl ring substituent is at the para position.

12. The compound of claim 3 wherein R$_2$ is represented by the following structural formula:

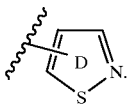

13. The compound of claim 1 wherein the compound is represented by the following structural formula:

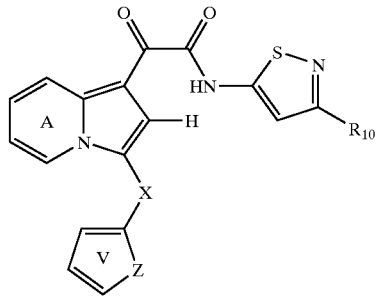

wherein:
Rings A and V are independently substituted or unsubstituted;
X is —CH$_2$—, —CH(CH$_3$)—, —O—, —NH— or —NCH$_3$—, and
R$_{10}$ is —H, an unsubstituted aliphatic group or a substituted aliphatic group.

14. The compound of claim 13 wherein Ring A is unsubstituted or substituted with —F, —Cl, —Br, —C1–C4 alkyl, C1–C4 alkoxy, —C1–C4 haloalkyl, C1–C4 haloalkoxy, —NH$_2$ or —CN; Ring V is substituted with one or more groups selected from —CH$_3$, —CH$_2$CH$_3$, —F, —Cl, —CN, and —OCH$_3$; and R$_{10}$ is —H, methyl or ethyl.

15. The compound of claim 14 wherein Ring A is unsubstituted, Ring V is substituted with one or more groups R$_{11}$; and each R$_{11}$ is independently —CH$_3$, —CH$_2$CH$_3$, —OCH$_3$, —F, —Cl or —CN.

16. A compound represented by the following structural formula:

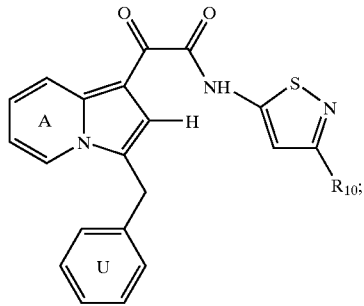

or a pharmaceutically acceptable salt thereof, wherein Rings A and U are independently substituted or unsubstituted and R$_{10}$ is —H, an unsttbsitured aliphatic group or a substituted aliphatic group.

17. The compound of claim 16 wherein Ring A is unsubstituted or substituted with —F, —Cl, —Br, —C1–C4 alkyl, C1–C4 alkoxy, —C1–C4 haloalkyl, C1–C4 haloalkoxy, —NH$_2$ or —CN; Ring U is substituted with one or more groups selected from —CH$_3$, —CH$_2$CH$_3$, —F, —Cl, —CN, and —OCH$_3$; and R$_{10}$ is —H, methyl or ethyl.

18. The compound of claim 17 wherein Ring U is monosubstituted with —CH$_3$, —CH$_2$CH$_3$, —F, —Cl, —CN or —OCH$_3$; and the Ring U substituent is in the para position.

19. A compound represented by the following structural formula:

[chemical structure]

or a pharmaceutically acceptable salt thereof, wherein $R_{11}$ is —$CH_3$, —$CH_2C_3$, —$OCH_3$, —F, —Cl or —CN.

20. A method of treating a subject with cancer comprising administering to the subject an effective amount of a compound represented by the following structural formula:

[chemical structure]

or a pharmaceutically acceptable salts thereof, wherein:
Ring A is substituted or unsubstituted and is optionally fused to an aryl group;
$Z_1$ and $Z_2$ are independently =O, =S, =N—$OR_{12}$ or $NR_{12}$;
$R_1$ and $R_2$ are independently —H, an aliphatic group, a substituted aliphatic group, or an unsubstituted aryl group or a substituted aryl group selected from:

[chemical structures labeled D, E, M, and N]

provided that $R_1$ and $R_2$ are not both —H;
$R_3$ is a substituted or unsubstituted aliphatic group or a substituted or unsubstituted aryl group represented by Ring V:

[chemical structure]

wherein Z is —O—, —S—, —NR—, or —CH=CH— and R is —H or C1–C4 alkyl;

X is a covalent bond, —C($R_4R_5$)—, —N($R_4$)—, —O—, —S—, —S(O)—, —S(O)$_2$—, —C(=O)—, —C(=O)—N($R_4$)—, or —N($R_4$)—C(=O)—;

$R_4$ and $R_5$ are independently —H or a substituted or unsubstituted aliphatic group; and $R_{12}$ is —H or a substituted or unsubstituted alkyl group.

21. The method of claim 20 wherein: Ring A substituted or unsubstituted, $Z_1$ and $Z_2$ are both =O; $R_1$ is —H; $R_2$ is a substituted or unsubstituted alkyl or aryl group, $R_3$ is a substituted or unsubstituted aryl group; and X is —C($R_{4R5}$)—, —N($R_4$)— or —O—.

22. The method of claim 21 wherein Rings D, E, M, and N are independently unsubstituted or substituted with a group independently selected from —OH, —Br, —Cl, —I, —F, —$OR^a$, —O—$COR^a$, —$COR^a$, —CN, —$NO_2$, —COOH, —$SO_3H$, —$NH_2$, —$NHR^a$, —N($R_aR^b$), —$COOR^a$, —CHO, —$CONH_2$, —$CONHR^a$, —CON($R^aR^b$), —$NHCOR^a$, —$NRCOR^a$, —$NHCONH_2$, —$NHCONR^aH$, —$NHCON(R^aR^b)$, —$NR^cCONH_2$, —$NR^cCONR^aH$, —$NR^cCON(R^aR^b)$, —C(=NH)—$NH_2$, —C(=NH)—$NHR^a$, —C(=NH)—N($R^aR^b$), —C(=$NR^c$)—$NH_2$, —C(=$NR^c$)—$NH^a$, —C(=$NR^c$)—N($R^aR^b$), —NH—C(=NH)—$NH_2$, —NH—C(=NH)—$NHR^a$, —NH—C(=NH)—N($R^aR^b$), —NH—C(=$NR^c$)—$NH_2$, NH—C(=$NR^c$)—$NHR^a$, —NH—C(=$NR^c$)—N($R^aR^b$), —$NR^dH$—C(=NH)—$NH_2$, —$NR^d$—C(=NH)—$NHR^a$, —$NR^d$—C(=NH)—N($R^aR^b$), —$NR^d$—C(=$NR^c$)—$NH_2$, —$NR^d$—C(=$NR^c$)—$NHR^a$, —$NR^d$—C(=$NR^c$)—N($R^aR^b$), —$NHNH_2$, —$NHNHR^a$, —$NHR^AR^b$, —$SO_2NH_2$, —$SO_2NHR^a$, —$SO_2NR^aR^b$, —CH=$CHR^a$, —CH=$CR^aR^b$, —$CR^c$=$CR^aR^b$, —$CR^c$=$CHR^a$, —$CR^c$=$CR^aR^b$, —$CCR^a$, —SH, —$SR^a$, —S(O)$R^a$, —S(O)$_2R^a$, alkyl groups, substituted alkyl group, benzyl group, substituted benzyl group, aryl group and substituted aryl group; wherein $R^a$—$R^d$ are each independently an alkyl group, substituted alkyl group, benzyl, substituted benzyl, aryl or substituted aryl group.

23. The method of claim 21 wherein Rings D, E, M, and N are independently unsubstituted or substituted with group selected form C1–C4 alkyl, C1–C4 hydroxyalkyl, —NH(C1–C4 alkyl), —N(C1–C4 alkyl)$_2$, —C(O)$NH_2$, —C(O)NH(C1–C4 alkyl), C(O)N(C1–C4 alkyl)$_2$, —NHC(O)(C1–C4 alkyl), —$NO_2$, C1–C4 alkoxy, —C(O)O—$CH_2CH_2$—NH(C1–C4 alkyl), —C(O)O—$CH_2CH_2$—N(C1–C4 alkyl)$_2$,

[chemical structures]

—NH-(phenyl), —$NH_2$, —$CH_2NH$—C(O)—O—(C1–C4 alkyl), —$CH_2NH_2$, —Cl, —F, —C(O)—O—(C1–C4 alkyl), —C(O)—NH—(C1–C4 alkyl), C3–C7 cycloalkyl, phenyl, —S—(C1–C4 alkyl), —CN, furyl, —S(O)$_2$—(C1–C4 alkyl), —S(O)$_2$—$NH_2$, —S(O)$_2$—NH(C1–C4 alkyl), and —S(O)$_2$—N(C1–C4 alkyl)$_2$.

24. The method of claim 23 wherein $R_2$ is represented by a structural formula selected from:

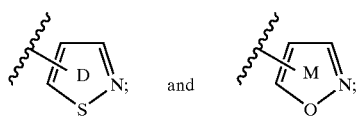

and $R_6$ is —H or a substituted or unsubstituted alkyl group.

25. The method of claim 24 wherein $R_2$ is represented by a structural formula selected from:

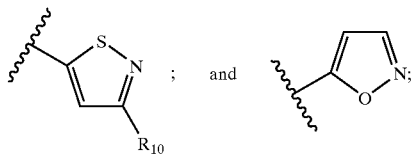

wherein:

$R_{10}$ is —H or an alkyl group.

26. The method of claim 25 wherein Ring A is optionally substituted with one or more groups selected front —F, —Cl, —Br, —C1–C4 alkyl, C1–C4 alkoxy, —C1–C4 haloalkyl, C1–C4 haloalkoxy, —NH$_2$ and —CN.

27. The method of claim 26 wherein Ring A is unsubstituted; $R_3$ is a phenyl group substituted with one or more substituents selected from —Br, —Cl, —F, —R$^e$, —OR$^e$, —CN, —COOR$^e$, —N(R$^e$)$_2$, —CON(R$^e$)$_2$, —NR$^e$COR$^f$, —NHCONH$_2$, and —SO$_2$N(R$^e$)$_2$; and each R$^e$ and R$^f$ are independently —H, an alkyl group or a substituted alkyl group.

28. The method of claim 27 wherein $R_3$ is a phenyl ring substituted with one or more substituents selected from —Cl, —F, —R$^e$, —OR$^e$, —CN, —NH$_2$, —CONH$_2$ and —NHCOR$^f$.

29. The method of claim 29 wherein $R_3$ is a phenyl ring substituted wit one or more substituents selected from —CH$_3$, —CH$_2$CH$_3$, —OCH$_3$, —CN, —F and —Cl.

30. The method of claim 28 wherein $R_3$ is a phenyl ring monosubstituted with —CH$_3$, —CH$_2$CH$_3$, —OCH$_3$, —CN, —F or —Cl; and wherein the phenyl ring substituent is at the para position.

31. The method of claim 20 wherein the compound is represented by the following structural formula:

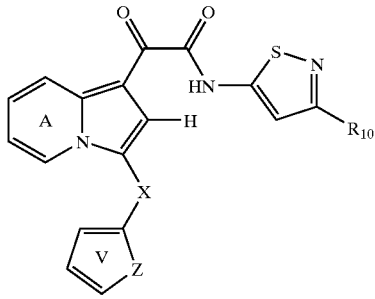

wherein:

Rings A and V are independently substituted or unsubstituted;

X is —CH$_2$—, —CH(CH$_3$)—, —O—, —NH— or —NCH$_3$—; and $R_{10}$ is —H, an unsubstituted aliphatic group or a substituted aliphatic group.

32. The method of claim 31 wherein Ring A is unsubstituted or substituted with —F, —Cl, —Br, —C1–C4 alkyl, C1–C4 alkoxy, —C1–C4 haloalkyl, C1–C4 haloalkoxy, —NH$_2$ or —CN; Ring U is substituted with one or more groups selected from —CH$_3$, —CH$_2$CH$_3$, —F, —Cl, —CN, and —OCH$_3$; and $R_{10}$ is —H, methyl or ethyl.

33. The method of claim 32 wherein Ring A is unsubstituted, Ring V is substituted with one or more groups $R_{11}$ and each $R_{11}$ is independently —CH$_3$, —CH$_2$CH$_3$, —OCH$_3$, —F, —Cl or —CN.

34. The method of claim 21 wherein $R_2$ is represented by the following structural formula:

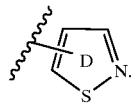

35. A method of treating a subject with cancer comprising administering to the subject a compound represented by the following structural formula:

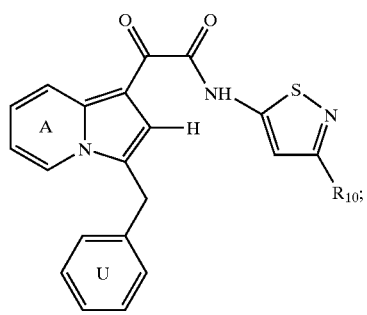

or a pharmaceutically acceptable salts thereof, wherein Rings A and U are independently substituted or unsubstituted and $R_{10}$ is —H, an unsubstituted aliphatic group or a substituted aliphatic group.

36. The method of claim 35 wherein Ring A is unsubstituted or substituted wit one or more substituents selected from —F, —Cl, —Br, —C1–C4 alkyl, C1–C4 alkoxy, —C1–C4 haloalkyl, C1–C4 haloalkoxy, —NH$_2$ and —CN; Ring U is substituted with one or more groups selected from —CH$_3$, —CH$_2$CH$_3$, —F, —Cl, and —OCH$_3$; and $R_{10}$ is —H, methyl or ethyl.

37. The method of claim 36 wherein Ring U is monosubstituted with —CH$_3$, —CH$_2$CH$_3$, —F, —Cl, —CN, or —OCH$_3$; and the Ring U substituent is at the para position.

38. A method of treating a subject with cancer comprising administering to the subject a compound represented by the following structural formula:

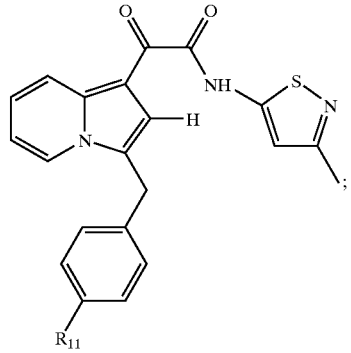

or a pharmaceutically acceptable salt thereof, wherein $R_{11}$ is —CH$_3$, —CH$_2$CH$_3$, —OCH$_3$, —F, —Cl or —CN.

39. A compound represented by one of the following structural formulas, or a pharmaceutically acceptable salt thereof:
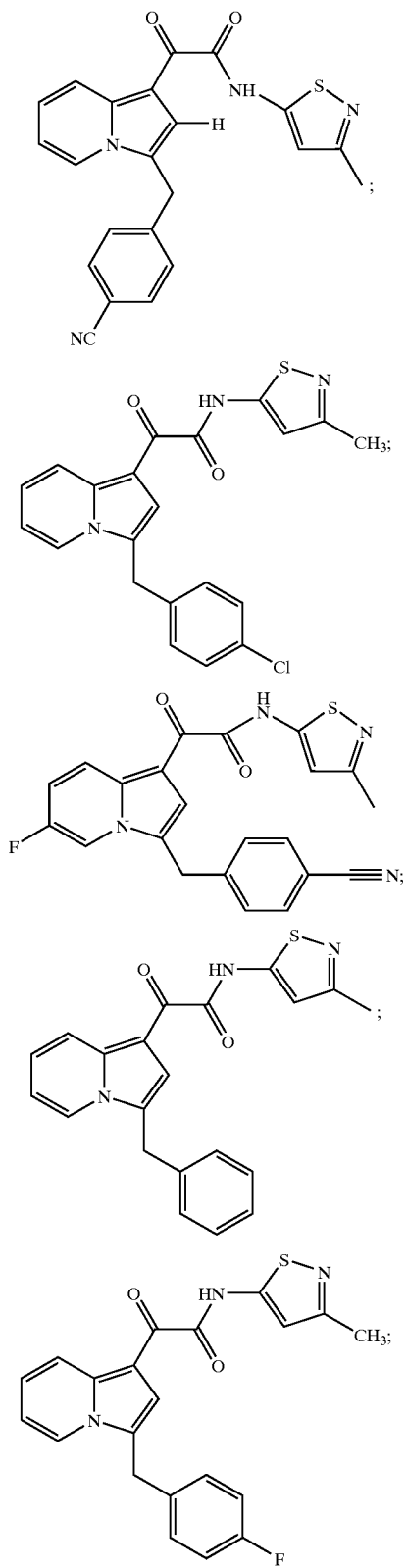
-continued
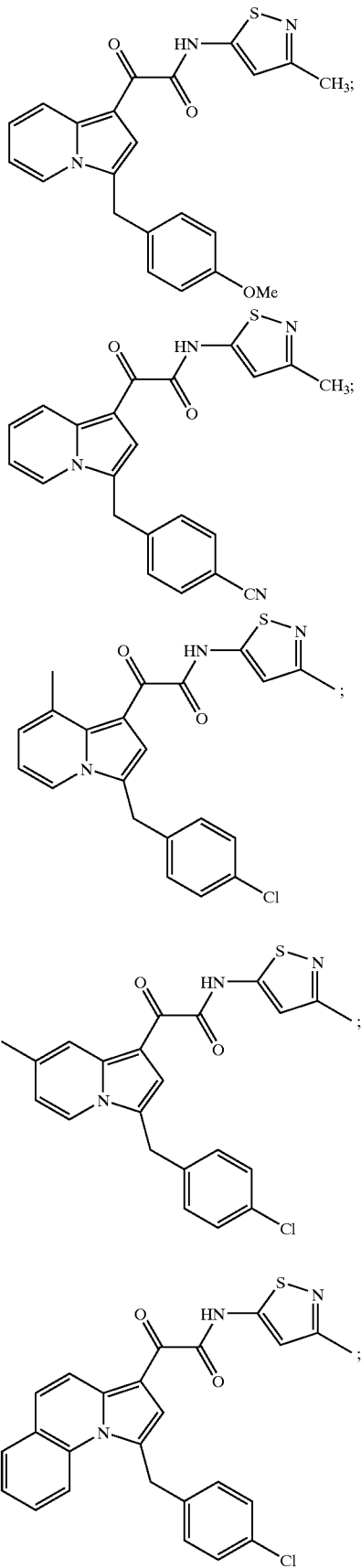

-continued
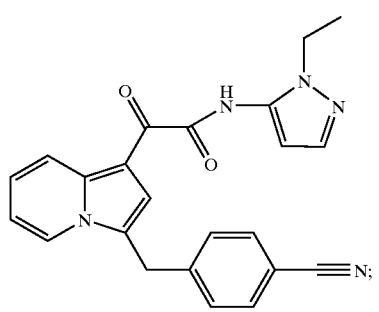
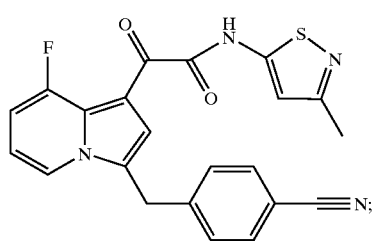
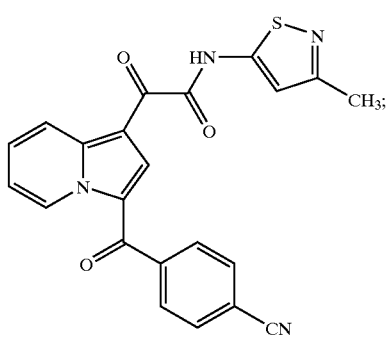
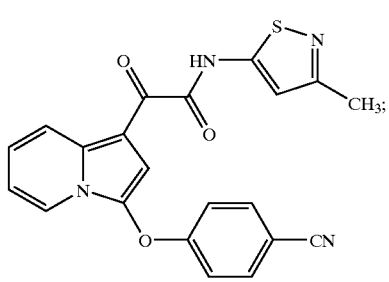
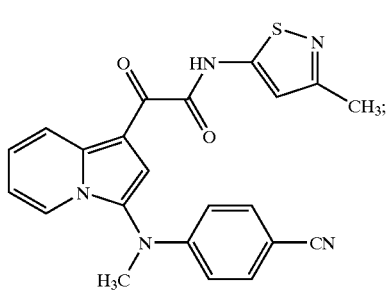
-continued
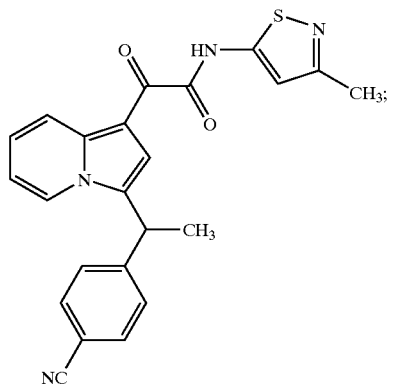
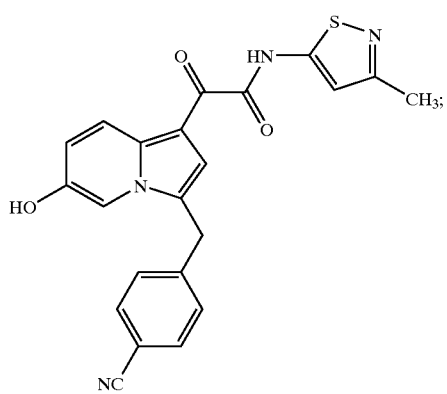
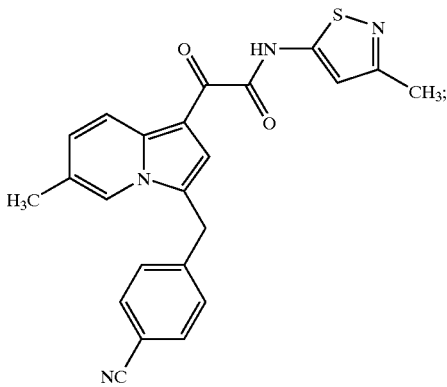
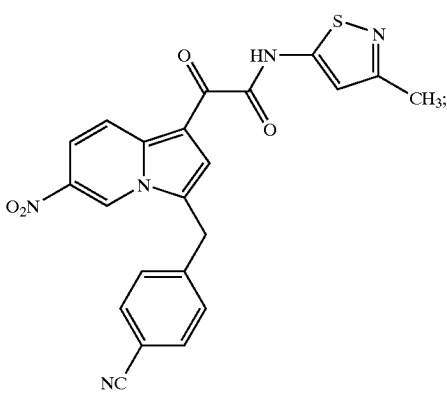

-continued

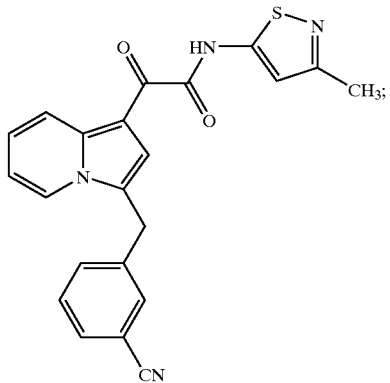

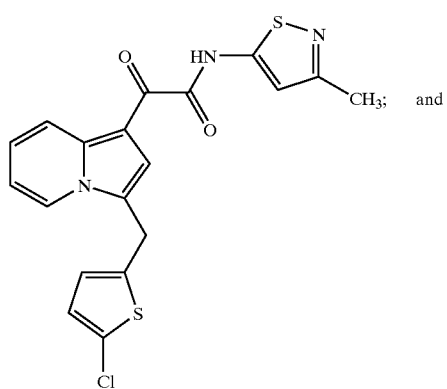 and

-continued

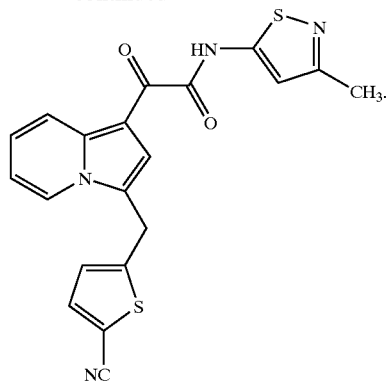

40. A method of treating a subject with cancer, comprising administering to the subject an effective amount of the compound of claim 39.

41. A compound represented by the following structural formula, or a pharmaceutically acceptable salt thereof:

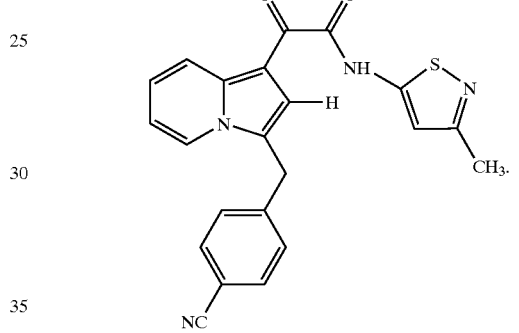

42. A method of treating a subject with cancer, comprising administering to the subject an effective amount of the compound of claim 41.

* * * * *

UNITED STATES PATENT AND TRADEMARK OFFICE
CERTIFICATE OF CORRECTION

PATENT NO. : 6,861,436 B2
DATED : March 1, 2005
INVENTOR(S) : Keizo Koya et al.

It is certified that error appears in the above-identified patent and that said Letters Patent is hereby corrected as shown below:

Column 38,
Line 31, delete the comma "," at the end of the line and insert -- ; --;
Line 37, delete "$R_3$" and insert -- $R_2$ --;
Line 37, delete "$R_1$" and insert -- $R_3$ --;
Line 47, delete "NCONR$^a$H" and insert -- NHCONR$^a$H -- ;
Line 57, delete "NHNHR$_a$" and insert -- NHNHR$^a$ --;
Line 57, delete "NH$^a$R$^b$" and insert -- NR$^a$R$^b$ --;
Line 61, delete "-S(O$_2$R$^a$" and insert -- -S(0)$_2$R$^a$ -- ;

Column 39,
Line 15, delete "-C(O)-N-(C1C4 alkyl)," and insert -- -C(O)-N-(C1-C4 alkyl), --
Line 49, delete "-N(R$^e$)$_2$" and insert -- N(R$^e$)$_2$, --;
Line 50, delete "(R$^e$)" and insert -- (R$^e$)$_2$ -- ;
Line 63, delete "wit" and insert -- with --;
Line 64, delete "-C13" and insert -- -Cl --;
Line 65, the word "para" should be in italics;

Column 40,
Line 55, delete "unsttbstitured" and insert -- unsubstituted --;
Line 66, the work "para" should be in italics;

Column 41,
Line 20, delete "-CH$_2$C$_3$," and insert -- CH$_2$CH$_3$, --;

Column 42,
Line 2, delete " -S(O)$_2$" and insert -- -S(O)$_2$- --;
Line 13, delete "-C(R$_{4R5}$)-" and insert -- -C(R$_4$R$_5$)- --;
Line 18, delete "-N(R$_a$R$^b$)" and insert -- -N(R$^a$R$^b$) --;
Line 25, delete "-C(=NR$^c$)-NH$^a$" and insert -- -C(=NR$^c$)-NHR$^a$ --;
Line 32, delete "NHR$^A$R$^b$"and insert -- -NHR$^a$R$^b$ --;
Line 43, delete "with group" and insert -- with a group --;
Line 44, delete "form" and insert -- from --;

Column 43,
Line 22, delete "front" and insert -- from --;
Line 37, delete "wit" and insert -- with --;
Line 42, the word "para" should be in italics;

UNITED STATES PATENT AND TRADEMARK OFFICE
CERTIFICATE OF CORRECTION

PATENT NO. : 6,861,436 B2
DATED : March 1, 2005
INVENTOR(S) : Keizo Koya et al.

It is certified that error appears in the above-identified patent and that said Letters Patent is hereby corrected as shown below:

Column 44,
Line 39, delete "wit" and insert -- with --;
Line 43, after "-Cl," insert -- -CN, --;
Line 46, the word "para" should be in italics;

Signed and Sealed this

Twenty-first Day of June, 2005

JON W. DUDAS
*Director of the United States Patent and Trademark Office*